(12) United States Patent
Campeta et al.

(10) Patent No.: US 8,791,140 B2
(45) Date of Patent: Jul. 29, 2014

(54) CRYSTALLINE FORMS OF 6-[2-(METHYLCARBAMOYL)PHENYL-SULFANYL]-3-E-[2-(PYRIDIN-2-YL) ETHENYONDAZOLE SUITABLE FOR THE TREATMENT OF ABNORMAL CELL GROWTH IN MAMMALS

(75) Inventors: Anthony Michael Campeta, Ledyard, CT (US); Brian Patrick Chekal, Niantic, CT (US); Robert Alan Singer, Niantic, CT (US)

(73) Assignee: Pfizer Inc., New York, NY (US)

( * ) Notice: Subject to any disclaimer, the term of this patent is extended or adjusted under 35 U.S.C. 154(b) by 863 days.

(21) Appl. No.: 12/594,575

(22) PCT Filed: Mar. 25, 2008

(86) PCT No.: PCT/IB2008/000792
§ 371 (c)(1),
(2), (4) Date: Apr. 1, 2010

(87) PCT Pub. No.: WO2008/122858
PCT Pub. Date: Oct. 16, 2008

(65) Prior Publication Data
US 2010/0179329 A1    Jul. 15, 2010

Related U.S. Application Data

(60) Provisional application No. 61/031,554, filed on Feb. 26, 2008, provisional application No. 60/976,546, filed on Oct. 1, 2007, provisional application No. 60/910,379, filed on Apr. 5, 2007.

(51) Int. Cl.
*A61K 31/4439* (2006.01)
*C07D 401/06* (2006.01)

(52) U.S. Cl.
USPC ........................................ 514/338; 546/275.7

(58) Field of Classification Search
USPC ........................................ 546/275.7; 514/338
See application file for complete search history.

(56) References Cited

U.S. PATENT DOCUMENTS

| | | | |
|---|---|---|---|
| 6,531,491 B1 | 3/2003 | Kania et al. | |
| 6,534,524 B1 | 3/2003 | Kania et al. | |
| 6,627,646 B2 * | 9/2003 | Bakale et al. | 514/322 |
| 6,884,890 B2 | 4/2005 | Kania et al. | |
| 7,141,581 B2 | 11/2006 | Bender et al. | |
| 7,141,587 B2 | 11/2006 | Kania et al. | |
| 7,232,910 B2 | 6/2007 | Ewanicki et al. | |
| 2004/0224988 A1 | 11/2004 | Freddo et al. | |
| 2006/0091067 A1 | 5/2006 | Fan et al. | |
| 2006/0094763 A1 | 5/2006 | Ye et al. | |
| 2007/0203196 A1 | 8/2007 | Ewanicki et al. | |

FOREIGN PATENT DOCUMENTS

WO  WO 2006/048745 A1  5/2006
WO  WO 2006/123223 A1  11/2006

OTHER PUBLICATIONS

Chemical & Engineering News, Feb. 2003, 32-35.*
Brittain ed., "Polymorphism in Pharmaceutical Science.," NY:Marcel Dekker, Inc., 1999, 1-2, 183-226, 235-238.*
U.S. Pharmacopia #23, National Formulary #18, 1995, 1843-1844.*
Muzaffar et al., "Polymorphism and Drug Availability, etc.," J of Pharm. (Lahore), 1979, 1(1), 59-66.*
Jain et al., "Polymorphism in Pharmacy", Indian Drugs, 1986, 23(6) 315-329.*
Taday et al., "Using Terahertz, etc.," J of Pharm. Sci., 92(4), 2003, 831-838.*
Concise Encyclopedia Chemistry, NY: Walter de Gruyter, 1993, 872-873.*
Ulicky. Comprehensive Dictionary of Physical Chemistry, NY: Prentice Hall, 1992, p. 21.*
Doelker, english translation of Ann. Pharm. Fr., 2002, 60: 161-176, pp. 1-39.*
Doelker, english translation of S.T.P, Pratiques (1999), 9(5), 399-409, pp. 1033.*
Otuska et al., "Effect of Polymorphic, etc.," Chem. Pharm. Bull., 47(6) 852-856 (1999).*
CMU Pharmaceutical polymorphism, internet, p. 1-3 (2002) (print out Apr. 3, 2008).*
Singhal et al., "Drug Polymorphism, etc.," Advanced Drug Delivery reviews 56, p. 335-347 (2004).*

* cited by examiner

*Primary Examiner* — Patricia L Morris
(74) *Attorney, Agent, or Firm* — Suzanne M. Bates; Matthew J. Pugmire; Stephen D. Prodnuk

(57) ABSTRACT

The present invention relates to crystalline polymorphic and amorphous form of 6-[2-(methylcarbamoyl)phenyl sulfanyl]-3-E-[2-(pyridin-2-yl)ethenyl]indazole and to methods for their preparation. The invention is also directed to pharmaceutical compositions containing at least one polymorphic form and to the therapeutic or prophylactic use of such polymorphic forms and compositions.

6 Claims, 16 Drawing Sheets

CRYSTALLINE FORMS OF 6-[2-(METHYLCARBAMOYL)PHENYL-SULFANYL]-3-E-[2-(PYRIDIN-2-YL) ETHENYONDAZOLE SUITABLE FOR THE TREATMENT OF ABNORMAL CELL GROWTH IN MAMMALS

CROSS-REFERENCE TO RELATED APPLICATIONS

This application is a §371 filing of PCT/IB2008/000792 filed Mar. 25, 2008, which claims the benefit of priority to U.S. Provisional Application No. 60/910,379, filed Apr. 5, 2007; U.S. Provisional Application No. 60/976,546 filed Oct. 1, 2007; and U.S. Provisional Application No. 61/031,554 filed Feb. 26, 2008; the entire contents of which are incorporated herein by reference.

FIELD OF THE INVENTION

The present invention relates to novel polymorphic forms of 6-[2-(methylcarbamoyl)phenylsulfanyl]-3-E-[2-(pyridin-2-yl)ethenyl]indazole and to methods for their preparation. The invention is also directed to pharmaceutical compositions containing at least one polymorphic form and to the therapeutic or prophylactic use of such polymorphic forms and compositions.

BACKGROUND OF THE INVENTION

This invention relates to novel polymorphic forms of 6-[2-(methylcarbamoyl)phenylsulfanyl]-3-E-[2-(pyridin-2-yl)ethenyl]indazole (also referred to as "Compound 1")

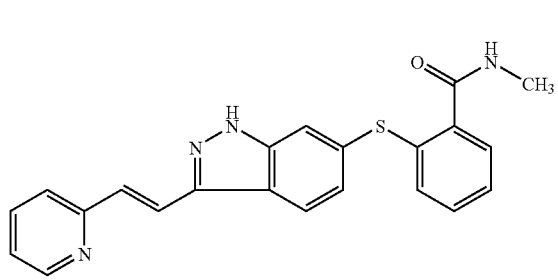

that are useful in the treatment of abnormal cell growth, such as cancer, in mammals. This invention also relates to compositions including such polymorphic forms, and to methods of using such compositions in the treatment of abnormal cell growth in mammals, especially humans.

Compound 1, as well as pharmaceutically acceptable salts thereof, are described in U.S. Pat. No. 6,534,524 and U.S. Pat. No. 6,531,491. Methods of making Compound 1 are described in U.S. Pat. No. 7,232,910 and U.S. Application Publication Nos. 2006-0091067 and 2007-0203196 and in WIPO International Publication No. WO 2006/048745. Polymorphic forms and pharmaceutical compositions of Compound 1 are also described in U.S. Application Publication No. 2006-0094763 and WIPO International Publication No. WO 2006/123223. Dosage forms of Compound 1 is also described in U.S. Application Publication No. 2004-0224988.

Compound 1 is a potent and selective inhibitor of vascular endothelial growth factor (VEGF)/platelet-derived growth factor (PDGF) receptor tyrosine kinase (RTK) being developed for use in early to late stage cancers. Protein tyrosine kinases have been identified as crucial targets in the therapeutic treatment of cancer. Growth factor ligands and their respective RTKs are required for tumor angiogenesis and growth. VEGF and PDGF are critical components in the process leading to the branching, extension, and survival of endothelial cells forming new blood vessels during angiogenesis. Unwanted angiogenesis is a hallmark of several diseases, such as retinopathies, psoriasis, rheumatoid arthritis, age-related macular degeneration (AMD), and cancer (including solid tumors) Folkman, *Nature Med.*, 1, 27-31 (1995).

As understood by those skilled in the art, it is desirable to have crystalline or amorphous forms, that possess physical properties amenable to reliable formulation and manufacture. Such properties include filterability, hygroscopicity, and flow, as well as stability to heat, moisture, and light.

Polymorphs are different crystalline forms of the same compound. The term polymorph may or may not include other solid state molecular forms including hydrates (e.g., bound water present in the crystalline structure) and solvates (e.g., bound solvents other than water) of the same compound. Crystalline polymorphs typically have different crystal structures due to a different packing of the molecules in the lattice. This results in a different crystal symmetry and/or unit cell parameters which directly influences its physical properties such as the X-ray diffraction characteristics of crystals or powders.

Polymorphic forms are of interest to the pharmaceutical industry and especially to those involved in the development of suitable dosage forms. If the polymorphic form is not held constant during clinical or stability studies, the exact dosage form used or studied may not be comparable from one lot to another. It is also desirable to have processes for producing a compound with the selected polymorphic form in high purity when the compound is used in clinical studies or commercial products since impurities present may produce undesired toxicological effects. Certain polymorphic forms may also exhibit enhanced thermodynamic stability or may be more readily manufactured in high purity in large quantities, and thus are more suitable for inclusion in pharmaceutical formulations. Certain polymorphs may display other advantageous physical properties such as lack of hygroscopic tendencies, improved solubility, and enhanced rates of dissolution due to different lattice energies.

The discussion of the background to the invention herein is included to explain the context of the present invention. This is not to be taken as an admission that any of the material referred to was published, known, or part of the common general knowledge in any country as of the priority date of any of the claims.

SUMMARY OF THE INVENTION

Although several polymorphs of Compound 1 have been identified, each polymorphic form can be uniquely identified by several different analytical parameters, alone or in combination, such as, but not limited to, powder X-ray diffraction pattern peaks or combinations of two or more peaks; solid state NMR $^{13}C$ and/or $^{15}N$ chemical shifts or combinations of two or more chemical shifts; Raman shift peaks or combinations of two or more Raman shift peaks; or combinations thereof.

One aspect of the present invention provides a crystalline form of 6-[2-(methylcarbamoyl)phenylsulfanyl]-3-E-[2-(pyridin-2-yl)ethenyl]indazole, represented as Compound 1

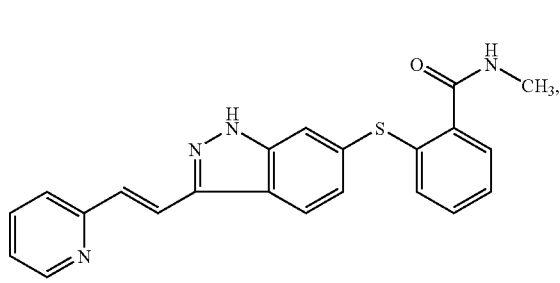

wherein said crystalline form is a polymorph of Form XXV. For example, in one embodiment, the present invention provides a crystalline form of Compound 1, wherein said crystalline form has a powder X-ray diffraction pattern comprising a peak at diffraction angle (2θ) of 5.1±0.1. In a further embodiment, the crystalline form has a powder X-ray diffraction pattern further comprising a peak at diffraction angle (2θ) of 15.9±0.1. In another embodiment, the crystalline form has a powder X-ray diffraction pattern further comprising peaks at diffraction angles (2θ) of 7.9±0.1, 10.7±0.1, and 18.2±0.1. In another embodiment, the crystalline form has a powder X-ray diffraction pattern further comprising peaks at diffraction angles (2θ) of 7.9±0.1, 15.9±0.1, and 18.2±0.1. In another embodiment, the crystalline form has a powder X-ray diffraction pattern further comprising peaks at diffraction angles (2θ) of 10.7±0.1, 15.9±0.1, and 26.2±0.1. In another embodiment, the crystalline form has a powder X-ray diffraction pattern further comprising peaks at diffraction angles (2θ) of 7.9±0.1, 10.7±0.1, 15.9±0.1, and 26.2±0.1. In another embodiment, the crystalline form has a powder X-ray diffraction pattern further comprising peaks at diffraction angles (2θ) of 7.9±0.1, 10.7±0.1, 15.9±0.1, 18.2±0.1, and 26.2±0.1.

Another aspect of the present invention provides a crystalline form of Compound 1, wherein said crystalline form has a powder X-ray diffraction pattern comprising peaks at diffraction angles (2θ) of 7.9±0.1, 10.7±0.1, and 18.2±0.1. Another aspect of the present invention provides a crystalline form of Compound 1, wherein said crystalline form has a powder X-ray diffraction pattern comprising peaks at diffraction angles (2θ) of 7.9±0.1, 15.9±0.1, and 18.2±0.1. Another aspect of the present invention provides a crystalline form of Compound 1, wherein said crystalline form has a powder X-ray diffraction pattern comprising peaks at diffraction angles (2θ) of 10.7±0.1, 15.9±0.1, and 26.2±0.1. Another aspect of the present invention provides a crystalline form of Compound 1, wherein said crystalline form has a powder X-ray diffraction pattern comprising peaks at diffraction angles (2θ) of 7.9±0.1, 10.7±0.1, 15.9±0.1, and 26.2±0.1

Another aspect of the present invention provides a crystalline form of Compound 1, wherein said crystalline form has a powder X-ray diffraction pattern comprising peaks at diffraction angles (2θ) essentially the same as shown in FIG. 1.

Another aspect of the present invention provides a crystalline form of Compound 1, wherein said crystalline form has a solid state NMR spectrum comprising $^{13}C$ chemical shifts at 167.4±0.2, 157.7±0.2, and 116.6±0.2 ppm.

Another aspect of the present invention provides a crystalline form of Compound 1, wherein said crystalline form has a solid state NMR spectrum comprising $^{13}C$ chemical shifts at 167.4±0.2, 157.7±0.2, 116.6±0.2 and 25.6±0.2 ppm.

Another aspect of the present invention provides a crystalline form of Compound 1, wherein said crystalline form has a solid state NMR spectrum comprising $^{13}C$ chemical shifts at positions essentially the same as shown in FIG. 2.

Another aspect of the present invention provides a crystalline form of Compound 1, wherein said crystalline form has a powder X-ray diffraction pattern comprising peaks at diffraction angles (2θ) of 5.1±0.1 and 15.9±0.1, and wherein said crystalline form has a solid state NMR spectrum comprising $^{13}C$ chemical shifts at 167.4±0.2, 157.7±0.2, and 116.6±0.2 ppm.

Another aspect of the present invention provides a crystalline form of Compound 1, wherein said crystalline form has a powder X-ray diffraction pattern comprising peaks at diffraction angles (2θ) of 5.1±0.1 and 15.9±0.1, and wherein said crystalline form has a solid state NMR spectrum comprising $^{13}C$ chemical shifts at 167.4±0.2, 157.7±0.2, 116.6±0.2 and 25.6±0.2 ppm.

Another aspect of the present invention provides a crystalline form of Compound 1, wherein said crystalline form has a powder X-ray diffraction pattern comprising peaks at diffraction angles (2θ) essentially the same as shown in FIG. 1, and wherein said crystalline form has a solid state NMR spectrum comprising $^{13}C$ chemical shifts at positions essentially the same as shown in FIG. 2.

Another aspect of the present invention provides a crystalline form of Compound 1, wherein said crystalline form has a Raman spectrum comprising Raman shift peaks ($cm^{-1}$) at positions essentially the same as shown in FIG. 3.

A further aspect of the present invention provides a crystalline form of Compound 1, wherein said crystalline form is a polymorph of Form XVI. For example, in one embodiment, the present invention provides a crystalline form of Compound 1, wherein said crystalline form has a powder X-ray diffraction pattern comprising peaks at diffraction angles (2θ) of 10.2±0.1, 10.6±0.1, and 16.8±0.1. In a further embodiment, the crystalline form has a powder X-ray diffraction pattern comprising peaks at diffraction angles (2θ) of 10.2±0.1, 10.6±0.1, and 17.9±0.1. In a further embodiment, the crystalline form has a powder X-ray diffraction pattern comprising peaks at diffraction angles (2θ) of 10.2±0.1, 10.6±0.1, and 18.2±0.1. In a further embodiment, the crystalline form has a powder X-ray diffraction pattern comprising peaks at diffraction angles (2θ) of 10.2±0.1, 10.6±0.1, and 25.4±0.1.

Another aspect of the present invention provides a crystalline form of Compound 1, wherein said crystalline form has a powder X-ray diffraction pattern comprising peaks at diffraction angles (2θ) essentially the same as shown in FIG. 4.

Another aspect of the present invention provides a crystalline form of Compound 1, wherein said crystalline form is a polymorph of Form XLI. For example, in one embodiment, the present invention provides a crystalline form of Compound 1, wherein said crystalline form has a powder X-ray diffraction pattern comprising a peak at diffraction angles (2θ) of 6.0±0.1 and 11.5±0.1.

In a further embodiment, the crystalline form has a powder X-ray diffraction pattern comprising a peak at diffraction angle (2θ) of 6.0±0.1 and 21.0±0.1.

In a further embodiment, the crystalline form has a powder X-ray diffraction pattern comprising a peak at diffraction angle (2θ) of 6.0±0.1 and 26.9±0.1.

In another embodiment, the crystalline form has a powder X-ray diffraction pattern comprising peaks at diffraction angles (2θ) of 6.0±0.1, 11.9±0.1 and 22.8±0.1.

In another embodiment, the crystalline form has a powder X-ray diffraction pattern comprising peaks at diffraction angles (2θ) of 11.9±0.1, 21.0±0.1 and 22.8±0.1.

In another embodiment, the crystalline form has a powder X-ray diffraction pattern comprising peaks at diffraction angles (2θ) of 11.9±0.1, 21.0±0.1 and 26.9±0.1.

In another embodiment, the crystalline form has a powder X-ray diffraction pattern comprising peaks at diffraction angles (2θ) of 11.9±0.1, 21.0±0.1 and 23.1±0.1.

In another embodiment, the crystalline form has a powder X-ray diffraction pattern comprising peaks at diffraction angles (2θ) of 11.5±0.1, 15.6±0.1 and 16.2±0.1.

In another embodiment, the crystalline form has a powder X-ray diffraction pattern comprising peaks at diffraction angles (2θ) of 11.5±0.1, 15.6±0.1 and 16.5±0.1.

Another aspect of the present invention provides a crystalline form of Compound 1, wherein said crystalline form has a powder X-ray diffraction pattern comprising peaks at diffraction angles (2θ) essentially the same as shown in FIG. 6.

Another aspect of the present invention provides a crystalline form of Compound 1, wherein said crystalline form has a solid state NMR spectrum comprising $^{13}C$ chemical shifts at 150.1±0.2, 136.6±0.2, 135.0±0.2, 116.9±0.2 and 27.5±0.2 ppm.

Another aspect of the present invention provides a crystalline form of Compound 1, wherein said crystalline form has a solid state NMR spectrum comprising $^{13}C$ chemical shifts at positions essentially the same as shown in FIG. 7.

Another aspect of the present invention provides a crystalline form of Compound 1, wherein said crystalline form has a solid state NMR spectrum comprising $^{15}N$ chemical shifts at −50.2±0.2, −79.0±0.2, −187.1±0.2 and −263.2±0.2 ppm.

Another aspect of the present invention provides a crystalline form of Compound 1, wherein said crystalline form has a solid state NMR spectrum comprising $^{15}N$ chemical shifts at positions essentially the same as shown in FIG. 8.

Another aspect of the present invention provides a crystalline form of Compound 1, wherein said crystalline form has a powder X-ray diffraction pattern comprising peaks at diffraction angles (2θ) of 6.0±0.1 and 11.5±0.1 and wherein said crystalline form has a solid state NMR spectrum comprising $^{13}C$ chemical shifts at 150.1±0.2 and 27.5±0.2 ppm.

Another aspect of the present invention provides a crystalline form of Compound 1, wherein said crystalline form has a powder X-ray diffraction pattern comprising peaks at diffraction angles (2θ) of 6.0±0.1, 11.5±0.1 and 11.9±0.1 and wherein said crystalline form has a solid state NMR spectrum comprising $^{13}C$ chemical shifts at 150.1±0.2, 136.6±0.2, 135.0±0.2, 116.9±0.2 and 27.5±0.2 ppm.

Another aspect of the present invention provides a crystalline form of Compound 1, wherein said crystalline form has a powder X-ray diffraction pattern comprising peaks at diffraction angles (2θ) essentially the same as shown in FIG. 6, and wherein said crystalline form has a solid state NMR spectrum comprising $^{13}C$ chemical shifts at positions essentially the same as shown in FIG. 7.

Another aspect of the present invention provides a crystalline form of Compound 1, wherein said crystalline form has a powder X-ray diffraction pattern comprising peaks at diffraction angles (2θ) essentially the same as shown in FIG. 6, and wherein said crystalline form has a solid state NMR spectrum comprising $^{15}N$ chemical shifts at positions essentially the same as shown in FIG. 8.

Another aspect of the present invention provides a crystalline form of Compound 1, wherein said crystalline form has a Raman spectrum comprising Raman shift peaks ($cm^{-1}$) at positions essentially the same as shown in FIG. 9.

A further aspect of the present invention provides a crystalline form of Compound 1, wherein said crystalline form is a polymorph of Form IX. For example, in one embodiment, the present invention provides a crystalline form of Compound 1, wherein said crystalline form has a powder X-ray diffraction pattern comprising peaks at diffraction angles (2θ) of 7.7±0.1, 8.1±0.1, 8.5±0.1 and 14.3±0.1. In another aspect, said crystalline form has a powder X-ray diffraction pattern comprising peaks at diffraction angles (2θ) of 7.7±0.1, 8.1±0.1, 8.5±0.1, and 18.3±0.1. In another aspect, said crystalline form of Compound 1 has a powder X-ray diffraction pattern comprising peaks at diffraction angles (2θ) essentially the same as shown in FIG. 10.

Another aspect of the present invention provides a crystalline form of Compound 1, wherein said substantially pure crystalline form has a solid state NMR spectrum comprising $^{13}C$ chemical shifts at 171.4±0.2 and 28.0±0.2 ppm. In another aspect, said crystalline form of Compound 1 has solid state NMR spectrum comprising $^{13}C$ chemical shifts at positions essentially the same as shown in FIG. 11.

Another aspect of the present invention provides a crystalline form of Compound 1, wherein said substantially pure crystalline form has a powder X-ray diffraction pattern comprising peaks at diffraction angles (2θ) essentially the same as shown in FIG. 10, and wherein said substantially pure crystalline form has a solid state NMR spectrum comprising $^{13}C$ chemical shifts at positions essentially the same as shown in FIG. 11.

A further aspect of the present invention provides a crystalline form of Compound 1, wherein said crystalline form is a polymorph of Form XII. For example, in one embodiment, the present invention provides a crystalline form of Compound 1, wherein said crystalline form has a powder X-ray diffraction pattern comprising peaks at diffraction angles (2θ) of 11.9±0.1, 18.1±0.1, and 31.2±0.1. In another embodiment, the present invention provides a crystalline form of Compound 1, wherein said crystalline form has a powder X-ray diffraction pattern comprising peaks at diffraction angles (2θ) of 11.9±0.1, 28.1±0.1, and 31.2±0.1. In another embodiment, the present invention provides a crystalline form of Compound 1, wherein said crystalline form has a powder X-ray diffraction pattern comprising peaks at diffraction angles (2θ) of 16.8±0.1, 28.1±0.1, and 31.2±0.1. In another embodiment, the present invention provides a crystalline form of Compound 1, wherein said crystalline form has a powder X-ray diffraction pattern comprising peaks at diffraction angles (2θ) of 25.3±0.1, 28.1±0.1, and 31.2±0.1.

Another aspect of the present invention provides a crystalline form of Compound 1, wherein said crystalline form has a powder X-ray diffraction pattern comprising peaks at diffraction angles (2θ) essentially the same as shown in FIG. 12.

A further aspect of the present invention provides a crystalline form of Compound 1, wherein said crystalline form is a polymorph of Form XV. For example, in one embodiment, the present invention provides a crystalline form of Compound 1, wherein said crystalline form has a powder X-ray diffraction pattern comprising peaks at diffraction angles (2θ) of 10.1±0.1, 11.9±0.1, 15.2±0.1, 21.5±0.1, and 26.3±0.1. In another embodiment, the present invention provides a crystalline form of Compound 1, wherein said crystalline form has a powder X-ray diffraction pattern comprising peaks at diffraction angles (2θ) of 10.1±0.1, 21.5±0.1, 25.0±0.1, and 25.3±0.1.

Another aspect of the present invention provides a crystalline form of Compound 1, wherein said crystalline form has a powder X-ray diffraction pattern comprising peaks at diffraction angles (2θ) essentially the same as shown in FIG. 13.

Another aspect of the present invention provides an amorphous form of Compound 1, wherein said amorphous form has a powder X-ray diffraction pattern comprising peaks at diffraction angles (2θ) essentially the same as shown in FIGS. 14 and 15.

Another aspect of the present invention provides an amorphous form of Compound 1, wherein said amorphous form has a solid state NMR spectrum comprising $^{13}C$ chemical shifts at positions essentially the same as shown in FIG. 16.

In a further aspect, the present invention contemplates that the crystalline forms of Compound 1 as described herein can exist in the presence of other crystalline or amorphous forms or mixtures thereof of Compound 1. Accordingly, in one embodiment, the present invention provides any of the crystalline forms of Compound 1 as described herein, wherein said crystalline form is present in a solid form that includes less than 95%, less than 90%, less than 80%, less than 70%, less than 60%, less than 50%, less than 40%, less than 30%, less than 20%, less than 10%, less than 5%, less than 3%, or less than 1% by weight of any other physical forms of Compound 1. For example, in one embodiment is a solid form of Compound 1 comprising a crystalline form of Compound 1 that has a powder X-ray diffraction pattern comprising a peak at diffraction angle (2θ) of 5.1±0.1, and wherein said solid form includes less than 95%, less than 90%, less than 80%, less than 70%, less than 60%, less than 50%, less than 40%, less than 30%, less than 20%, less than 10%, less than 5%, less than 3%, or less than 1% by weight of any other physical forms of Compound 1.

Further for example, the present invention provides a substantially pure crystalline form of Compound 1, wherein said substantially pure crystalline form has a powder X-ray diffraction pattern comprising a peak at diffraction angle (2θ) of 5.1±0.1. In a further embodiment, said substantially pure crystalline form has a powder X-ray diffraction pattern comprising peaks at diffraction angles (2θ) of 5.1±0.1 and 15.9±0.1. In a further embodiment, said substantially pure crystalline form has a powder X-ray diffraction pattern comprising peaks at diffraction angles (2θ) of 5.1±0.1, 7.9±0.1, 10.7±0.1, and 18.2±0.1. In a further embodiment, said substantially pure crystalline form has a powder X-ray diffraction pattern comprising peaks at diffraction angles (2θ) of 5.1±0.1, 7.9±0.1, 15.9±0.1, and 18.2±0.1. In a further embodiment, said substantially pure crystalline form has a powder X-ray diffraction pattern comprising peaks at diffraction angles (2θ) of 5.1±0.1, 10.7±0.1, 15.9±0.1, and 26.2±0.1. In a further embodiment, said substantially pure crystalline form has a powder X-ray diffraction pattern comprising peaks at diffraction angles (2θ) of 5.1±0.1, 7.9±0.1, 10.7±0.1, 15.9±0.1, and 26.2±0.1. In a further embodiment, said substantially pure crystalline form has a powder X-ray diffraction pattern comprising peaks at diffraction angles (2θ) of 5.1±0.1, 7.9±0.1, 10.7±0.1, 15.9±0.1, 18.2±0.1, and 26.2±0.1.

Another aspect of the present invention provides a substantially pure crystalline form of Compound 1, wherein said substantially pure crystalline form has a powder X-ray diffraction pattern comprising peaks at diffraction angles (2θ) essentially the same as shown in FIG. 1.

Another aspect of the present invention provides a substantially pure crystalline form of Compound 1, wherein said substantially pure crystalline form has a solid state NMR spectrum comprising $^{13}C$ chemical shifts at 167.4±0.2, 157.7±0.2, and 116.6±0.2 ppm.

Another aspect of the present invention provides a substantially pure crystalline form of Compound 1, wherein said substantially pure crystalline form has a solid state NMR spectrum comprising $^{13}C$ chemical shifts at 167.4±0.2, 157.7±0.2, 116.6±0.2 and 25.6±0.2 ppm.

Another aspect of the present invention provides a substantially pure crystalline form of Compound 1, wherein said substantially pure crystalline form has a solid state NMR spectrum comprising $^{13}C$ chemical shifts at positions essentially the same as shown in FIG. 2.

Another aspect of the present invention provides a substantially pure crystalline form of Compound 1, wherein said substantially pure crystalline form is a substantially pure polymorph of Form XXV.

Further for example, the present invention provides a substantially pure crystalline form of Compound 1, wherein said substantially pure crystalline form has a powder X-ray diffraction pattern comprising peaks at diffraction angles (2θ) of 10.2±0.1, 10.6±0.1, and 16.8±0.1. In a further embodiment, said substantially pure crystalline form has a powder X-ray diffraction pattern comprising peaks at diffraction angles (2θ) of 10.2±0.1, 10.6±0.1, and 17.9±0.1. In a further embodiment, said substantially pure crystalline form has a powder X-ray diffraction pattern comprising peaks at diffraction angles (2θ) of 10.2±0.1, 10.6±0.1, and 18.2±0.1. In a further embodiment, said substantially pure crystalline form has a powder X-ray diffraction pattern comprising peaks at diffraction angles (2θ) of 10.2±0.1, 10.6±0.1, and 25.4±0.1.

Another aspect of the present invention provides a substantially pure crystalline form of Compound 1 wherein said substantially pure crystalline form has a powder X-ray diffraction pattern comprising peaks at diffraction angles (2θ) essentially the same as shown in FIG. 4.

Another aspect of the present invention provides a substantially pure crystalline form of Compound 1, wherein said substantially pure crystalline form is polymorph of Form XVI.

Another aspect of the present invention provides a substantially pure crystalline form of Compound 1, wherein said substantially pure crystalline form is polymorph of Form XLI. For example, in one embodiment, the present invention provides a substantially pure crystalline form of Compound 1, wherein said substantially pure crystalline form has a powder X-ray diffraction pattern comprising a peak at diffraction angles (2θ) of 6.0±0.1 and 11.5±0.1.

In a further embodiment, the substantially pure crystalline form has a powder X-ray diffraction pattern comprising a peak at diffraction angle (2θ) of 6.0±0.1 and 21.0±0.1.

In a further embodiment, the substantially pure crystalline form has a powder X-ray diffraction pattern comprising a peak at diffraction angle (2θ) of 6.0±0.1 and 26.9±0.1.

In another embodiment, the substantially pure crystalline form has a powder X-ray diffraction pattern comprising peaks at diffraction angles (2θ) of 6.0±0.1, 11.9±0.1 and 22.8±0.1

In another embodiment, the substantially pure crystalline form has a powder X-ray diffraction pattern comprising peaks at diffraction angles (2θ) of 11.9±0.1, 21.0±0.1 and 22.8±0.1.

In another embodiment, the substantially pure crystalline form has a powder X-ray diffraction pattern comprising peaks at diffraction angles (2θ) of 11.9±0.1, 21.0±0.1 and 26.9±0.1.

In another embodiment, the substantially pure crystalline form has a powder X-ray diffraction pattern comprising peaks at diffraction angles (2θ) of 11.9±0.1, 21.0±0.1 and 23.1±0.1.

In another embodiment, the substantially pure crystalline form has a powder X-ray diffraction pattern comprising peaks at diffraction angles (2θ) of 11.5±0.1, 15.6±0.1 and 16.2±0.1.

In another embodiment, the substantially pure crystalline form has a powder X-ray diffraction pattern comprising peaks at diffraction angles (2θ) of 11.5±0.1, 15.6±0.1 and 16.5±0.1.

Another aspect of the present invention provides a substantially pure crystalline form of Compound 1, wherein said substantially pure crystalline form has a powder X-ray diffraction pattern comprising peaks at diffraction angles (2θ) essentially the same as shown in FIG. 6.

Another aspect of the present invention provides a substantially pure crystalline form of Compound 1, wherein said substantially pure crystalline form has a solid state NMR spectrum comprising $^{13}C$ chemical shifts at 150.1±0.2, 136.6±0.2, 135.0±0.2, 116.9±0.2 and 27.5±0.2 ppm.

Another aspect of the present invention provides a substantially pure crystalline form of Compound 1, wherein said substantially pure crystalline form has a solid state NMR spectrum comprising $^{13}C$ chemical shifts at positions essentially the same as shown in FIG. 7.

Another aspect of the present invention provides a substantially pure crystalline form of Compound 1, wherein said substantially pure crystalline form has a solid state NMR spectrum comprising $^{15}N$ chemical shifts at −50.2±0.2, −79.0±0.2, −187.1±0.2 and −263.2±0.2 ppm.

Another aspect of the present invention provides a substantially pure crystalline form of Compound 1, wherein said substantially pure crystalline form has a solid state NMR spectrum comprising $^{15}N$ chemical shifts at positions essentially the same as shown in FIG. 8.

Another aspect of the present invention provides a substantially pure crystalline form of Compound 1, wherein said substantially pure crystalline form has a powder X-ray diffraction pattern comprising peaks at diffraction angles (2θ) of 6.0±0.1, 11.5±0.1 and 11.9±0.1 and wherein said substantially pure crystalline form has a solid state NMR spectrum comprising $^{13}C$ chemical shifts at 150.1±0.2, 136.6±0.2, 135.0±0.2, 116.9±0.2 and 27.5±0.2 ppm.

Another aspect of the present invention provides a substantially pure crystalline form of Compound 1, wherein said substantially pure crystalline form has a powder X-ray diffraction pattern comprising peaks at diffraction angles (2θ) essentially the same as shown in FIG. 6, and wherein said substantially pure crystalline form has a solid state NMR spectrum comprising $^{13}C$ chemical shifts at positions essentially the same as shown in FIG. 7.

Another aspect of the present invention provides a substantially pure crystalline form of Compound 1, wherein said substantially pure crystalline form has a powder X-ray diffraction pattern comprising peaks at diffraction angles (2θ) essentially the same as shown in FIG. 6, and wherein said substantially pure crystalline form has a solid state NMR spectrum comprising $^{15}N$ chemical shifts at positions essentially the same as shown in FIG. 8.

Another aspect of the present invention provides a substantially pure crystalline form of Compound 1, wherein said substantially pure crystalline form has a Raman spectrum comprising Raman shift peaks ($cm^{-1}$) at positions essentially the same as shown in FIG. 9.

A further aspect of the present invention provides a substantially pure crystalline form of Compound 1, wherein said crystalline form is a polymorph of Form IX. For example, in one embodiment, the present invention provides a substantially pure crystalline form of Compound 1, wherein said substantially pure crystalline form has a powder X-ray diffraction pattern comprising peaks at diffraction angles (2θ) of 7.7±0.1, 8.1±0.1, 8.5±0.1 and 14.3±0.1. In a further embodiment, said substantially pure crystalline form has a powder X-ray diffraction pattern comprising peaks at diffraction angles (2θ) of 7.7±0.1, 8.1±0.1, 8.5±0.1, and 18.3±0.1.

Another aspect of the present invention provides a substantially pure crystalline form of Compound 1, wherein said substantially pure crystalline form has a solid state NMR spectrum comprising $^{13}C$ chemical shifts at 171.4±0.2 and 28.0±0.2 ppm.

Another aspect of the present invention provides a substantially pure crystalline form of Compound 1, wherein said substantially pure crystalline form has a powder X-ray diffraction pattern comprising peaks at diffraction angles (2θ) essentially the same as shown in FIG. 10, and wherein said substantially pure crystalline form has a solid state NMR spectrum comprising $^{13}C$ chemical shifts at positions essentially the same as shown in FIG. 11.

A further aspect of the present invention provides a substantially pure crystalline form of Compound 1, wherein said substantially pure crystalline form is a polymorph of Form XII. For example, in one embodiment, the present invention provides a substantially pure crystalline form of Compound 1, wherein said substantially pure crystalline form has a powder X-ray diffraction pattern comprising peaks at diffraction angles (2θ) of 11.9±0.1, 18.1±0.1, and 31.2±0.1. In another embodiment, the present invention provides a substantially pure crystalline form of Compound 1, wherein said substantially pure crystalline form has a powder X-ray diffraction pattern comprising peaks at diffraction angles (2θ) of 11.9±0.1, 28.1±0.1, and 31.2±0.1. In another embodiment, the present invention provides a substantially pure crystalline form of Compound 1, wherein said substantially pure crystalline form has a powder X-ray diffraction pattern comprising peaks at diffraction angles (2θ) of 16.8±0.1, 28.1±0.1, and 31.2±0.1. In another embodiment, the present invention provides a substantially pure crystalline form of Compound 1, wherein said substantially pure crystalline form has a powder X-ray diffraction pattern comprising peaks at diffraction angles (2θ) of 25.3±0.1, 28.1±0.1, and 31.2±0.1.

Another aspect of the present invention provides a substantially pure crystalline form of Compound 1, wherein said substantially pure crystalline form has a powder X-ray diffraction pattern comprising peaks at diffraction angles (2θ) essentially the same as shown in FIG. 12.

A further aspect of the present invention provides a substantially pure crystalline form of Compound 1, wherein said substantially pure crystalline form is a polymorph of Form XV. For example, in one embodiment, the present invention provides a substantially pure crystalline form of Compound 1, wherein said substantially pure crystalline form has a powder X-ray diffraction pattern comprising peaks at diffraction angles (2θ) of 10.1±0.1, 11.9±0.1, 15.2±0.1, 21.5±0.1, and 26.3±0.1. In another embodiment, the present invention provides a substantially pure crystalline form of Compound 1, wherein said substantially pure crystalline form has a powder X-ray diffraction pattern comprising peaks at diffraction angles (2θ) of 10.1±0.1, 21.5±0.1, 25.0±0.1, and 25.3±0.1.

Another aspect of the present invention provides a substantially pure crystalline form of Compound 1, wherein said substantially pure crystalline form has a powder X-ray diffraction pattern comprising peaks at diffraction angles (2θ) essentially the same as shown in FIG. 13.

Another aspect of the present invention provides a substantially pure amorphous form of Compound 1, wherein said substantially pure amorphous form has a powder X-ray diffraction pattern comprising peaks at diffraction angles (2θ) essentially the same as shown in FIG. 14. Another aspect of the present invention provides a substantially pure amorphous form of Compound 1, wherein said substantially pure amorphous form has a powder X-ray diffraction pattern comprising peaks at diffraction angles (2θ) essentially the same as shown in FIG. 15.

Another aspect of the present invention provides a substantially pure amorphous form of Compound 1, wherein said substantially pure amorphous form has a solid state NMR spectrum comprising $^{13}$C chemical shifts at positions essentially the same as shown in FIG. 16.

A further aspect of the present invention provides a pharmaceutical composition comprising any of the crystalline forms or amorphous forms of Compound 1 as described herein. In a further aspect, the invention provides an oral dosage form comprising any of the crystalline forms or amorphous forms of Compound 1 or pharmaceutical compositions described herein. For example, in one embodiment the oral dosage form is a tablet, pill, dragee core, or capsule. For example, in one embodiment, the oral dosage form is a tablet or capsule. Further, for example, in one embodiment the invention provides a tablet comprising any of the crystalline forms or amorphous forms of Compound 1 or pharmaceutical compositions described herein. For example, in one embodiment the tablet comprises from about 1 to about 10 mg of the crystalline form or amorphous form of Compound 1. Further, for example, the tablet comprises from about 1 to about 5 mg of the crystalline form or amorphous form of Compound 1. Even further, for example, the tablet comprises about 1 mg of the crystalline form or amorphous form of Compound 1. Even further, for example, the tablet comprises about 2 mg, about 3 mg, about 4 mg, or about 5 mg of the crystalline form or amorphous form of Compound 1. Even further for example, the crystalline form of Compound 1 is Form XXV. Still further, for example, the crystalline form of Compound 1 is Form XLI.

A further aspect of the present invention provides a method for preparing Compound 1 in crystalline Form XXV, said method comprising heating crystalline Form XVI of Compound 1. For example, in one embodiment, said heating is carried out in the presence of an appropriate solvent. In one embodiment, the solvent is ethanol. In a further embodiment, seed crystals of Form XXV are combined with crystalline Form XVI prior to, or during the heating.

A further aspect of the present invention provides a method for preparing Compound 1 in crystalline Form XVI, said method comprising dissolving Form VIII of Compound 1 in an appropriate solvent and heating.

A further aspect of the present invention provides a method for preparing Compound 1 in crystalline Form XLI, said method comprising heating crystalline Form XVI of Compound 1. For example, in one embodiment, said heating is carried out in the presence of an appropriate solvent. In one embodiment, the solvent is ethanol. In a further embodiment, seed crystals of Form XLI are combined with crystalline Form XVI prior to, or during the heating.

A further aspect of the present invention provides a method for preparing Compound 1 in amorphous from crystalline Form XLI, said method comprising grinding crystalline Form XLI of Compound 1. For example, in one embodiment, said grinding is carried out through ball milling.

A further aspect of the present invention provides a method of treating cancer in a mammal, the method comprising administering to the mammal a therapeutically effective amount of any of the crystalline forms of Compound 1 or any of the pharmaceutical compositions described herein.

In a particular aspect of any of the preceding method embodiments, the method further comprises administering one or more anti-tumor agents, anti-angiogenesis agents, signal transduction inhibitors, or antiproliferative agents.

DEFINITIONS

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of "treating" as defined immediately above.

As used herein, the term "Compound 1" means the chemical compound 6-[2-(methylcarbamoyl)phenylsulfanyl]-3-E-[2-(pyridin-2-yl)ethenyl]indazole, also represented by the structural formula

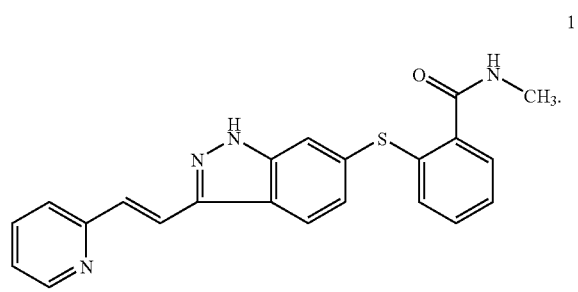

As used herein, the term "substantially pure" with reference to a particular crystalline or amorphous form means that the crystalline or amorphous form includes less than 10%, preferably less than 5%, preferably less than 3%, preferably less than 1% by weight of any other physical forms of the compound.

As used herein, the term "essentially the same" with reference to X-ray diffraction peak positions means that typical peak position and intensity variability are taken into account. For example, one skilled in the art will appreciate that the peak positions (2θ) will show some variability, typically as much as 0.1 to 0.2 degrees, depending on the solvents being used, as well as on the apparatus being used to measure the diffraction. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only. Similarly, as used herein, "essentially the same" with reference to solid state NMR spectra and Raman spectra is intended to also encompass the variabilities associated with these analytical techniques, which are known to those of skill in the art. For example, $^{13}$C chemical shifts measured in solid state NMR will typically have a variability of up to 0.2 ppm for well defined peaks, and even larger for broad lines, while Raman shifts will typically have a variability of about 2 cm$^{-1}$.

The term "polymorph" refers to different crystalline forms of the same compound and includes, but is not limited to, other solid state molecular forms including hydrates (e.g., bound water present in the crystalline structure) and solvates (e.g., bound solvents other than water) of the same compound.

The term "2 theta value" or "2θ" refers to the peak position in degrees based on the experimental setup of the X-ray diffraction experiment and is a common abscissa unit in diffraction patterns. The experimental setup requires that if a reflection is diffracted when the incoming beam forms an angle theta (θ) with a certain lattice plane, the reflected beam is recorded at an angle 2 theta (2θ). It should be understood that reference herein to specific 2θ values for a specific polymorphic form is intended to mean the 2θ values (in degrees) as measured using the X-ray diffraction experimental conditions as described herein. For example, as described herein, CuKα (wavelength 1.54056 Å) was used as the source of radiation.

The term "amorphous" refers to any solid substance which (i) lacks order in three dimensions, or (ii) exhibits order in less than three dimensions, order only over short distances (e.g., less than 10 Å), or both. Thus, amorphous substances include partially crystalline materials and crystalline mesophases with, e.g. one- or two-dimensional translational order (liquid crystals), orientational disorder (orientationally disordered crystals), or conformational disorder (conformationally disordered crystals). Amorphous solids may be characterized by known techniques, including X-ray powder diffraction (XRPD) crystallography, solid state nuclear magnet resonance (ssNMR) spectroscopy, differential scanning calorimetry (DSC), or some combination of these techniques. As illustrated, below, amorphous solids give diffuse XRPD patterns, typically comprised of one or two broad peaks (i.e., peaks having base widths of about 5° 2θ or greater).

The term "crystalline" refers to any solid substance exhibiting three-dimensional order, which in contrast to an amorphous solid substance, gives a distinctive XRPD pattern with sharply defined peaks.

The term "solvate" describes a molecular complex comprising the drug substance and a stoichiometric or non-stoichiometric amount of one or more solvent molecules (e.g., ethanol). When the solvent is tightly bound to the drug the resulting complex will have a well-defined stoichiometry that is independent of humidity. When, however, the solvent is weakly bound, as in channel solvates and hygroscopic compounds, the solvent content will be dependent on humidity and drying conditions. In such cases, the complex will often be non-stoichiometric.

The term "hydrate" describes a solvate comprising the drug substance and a stoichiometric or non-stoichiometric amount of water.

The term "powder X-ray diffraction pattern" or "PXRD pattern" refers to the experimentally observed diffractogram or parameters derived therefrom. Powder X-Ray diffraction patterns are characterized by peak position (abscissa) and peak intensities (ordinate).

The term "pharmaceutical composition" refers to a composition comprising one or more of the polymorphic forms of Compound 1 described herein, and other chemical components, such as physiologically/pharmaceutically acceptable carriers, diluents, vehicles and/or excipients. The purpose of a pharmaceutical composition is to facilitate administration of a compound to an organism, such as a human or other mammal.

The term "pharmaceutically acceptable" "carrier", "diluent", "vehicle", or "excipient" refers to a material (or materials) that may be included with a particular pharmaceutical agent to form a pharmaceutical composition, and may be solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

DETAILED DESCRIPTION OF THE INVENTION

Figure 1:
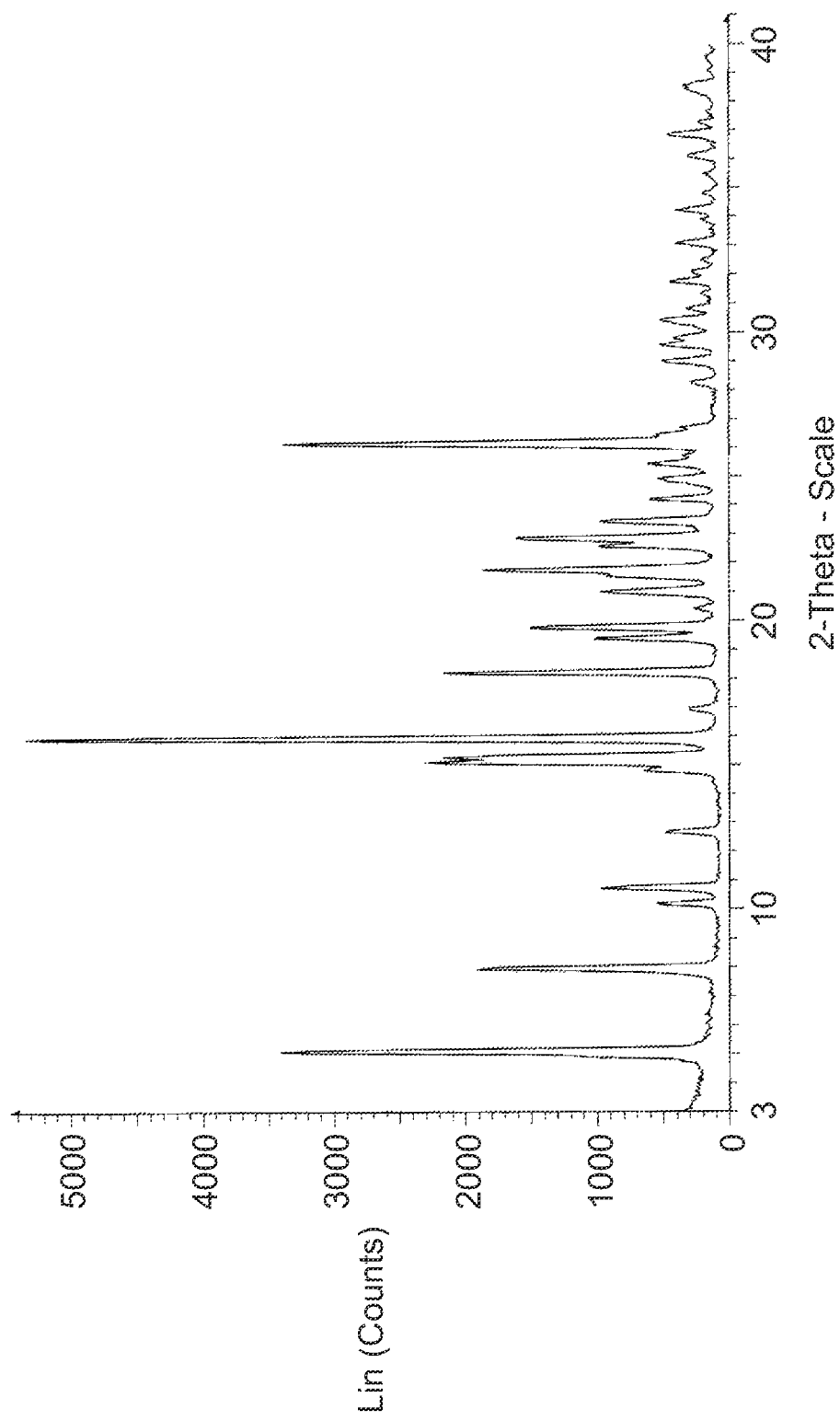
FIG. 1 shows a PXRD pattern of Compound 1 Form XXV carried out on a Bruker D5000 diffractometer.

It has been found that Compound 1 can exist in multiple crystalline forms (polymorphs) or as an amorphous form. These forms may be used in a formulated product for the treatment of hyperproliferative indications, including cancer. Each form may have advantages over the others in terms of properties such as bioavailability, stability, and manufacturability. Novel crystalline forms of Compound 1 have been discovered which are likely to be more suitable for bulk preparation and handling than other polymorphic forms. Processes for producing polymorphic forms of Compound 1 in high purity are described herein and in U.S. Application No. 2006-0094763. Another object of the present invention is to provide a process for the preparation of each polymorphic form of Compound 1, substantially free from other polymorphic forms of Compound 1. Additionally it is an object of the present invention to provide pharmaceutical formulations comprising Compound 1 in different polymorphic forms as discussed above, and methods of treating hyperproliferative conditions by administering such pharmaceutical formulations.

I. Polymorphic Forms of Compound 1

Each crystalline form of Compound 1 can be characterized by one or more of the following: powder X-ray diffraction pattern (i.e., X-ray diffraction peaks at various diffraction angles (2θ)), solid state nuclear magnetic resonance (NMR) spectral pattern, Raman spectral diagram pattern, aqueous solubility, light stability under International Conference on Harmonization (ICH) high intensity light conditions, and physical and chemical storage stability. For example, polymorphic Forms XXV, XVI, VIII, XLI, IX, XII, XV, and amorhous form (discussed below) of Compound 1 were each characterized by the positions and relative intensities of peaks in their powder X-ray diffraction patterns. The powder X-ray diffraction parameters differ for each of the polymorphic forms of Compound 1. For example, Forms XXV, XVI, VIII, XLI, IX, XII, XV, and amorhous form of Compound 1 can therefore be distinguished from each other and from other polymorphic forms of Compound 1 by using powder X-ray diffraction.

The powder X-ray diffraction patterns of the different polymorphic forms (Forms XXV, XVI, VIII, XLI, IX, XII, XV) and amorphous form of Compound 1 were carried out on a Bruker D5000 diffractometer using copper radiation (CuKα, wavelength: 1.54056 Å). The tube voltage and amperage were set to 40 kV and 40 mA, respectively. The divergence and scattering slits were set at 1 mm, and the receiving slit was set at 0.6 mm. Diffracted radiation was detected by a Kevex PSI detector. A theta-two theta continuous scan at 2.4 degrees/min (1 second/0.04 degree step) from 3.0 to 40 degrees 2θ was used. An alumina standard was analyzed to check the instrument alignment. Data were collected and analyzed using Bruker axis software Version 7.0. Samples were prepared by placing them in a quartz holder. It should be noted that Bruker Instruments purchased Siemans; thus, the Bruker D5000 instrument is essentially the same as a Siemans D5000. Eva Application 9.0.0.2 software was used to visualize and evaluate PXRD spectra. PXRD data files (.raw) of crystalline forms were not processed prior to peak searching. A polynomial smoothing factor of 0.3 was applied to the amorphous PXRD data file in one instance to enhance detail. Generally, a Threshold value of 1 and a Width value of 0.3 were used to make preliminary peak assignments. The output of automated assignments was visually checked to ensure validity and adjustments were manually made if necessary. These peak values for each form are summarized in tables below. PXRD data files of the amorphous form was To perform an X-ray diffraction measurement on a Bragg-Brentano instrument like the Bruker system used for measurements reported herein, the sample is typically placed into a holder which has a cavity. The sample powder is pressed by a glass slide or equivalent to ensure a random surface and proper sample height. The sample holder is then placed into the instrument. The incident X-ray beam is directed at the sample, initially at a small angle relative to the plane of the holder, and then moved through an arc that continuously increases the angle between the incident beam and the plane of the holder. Measurement differences associated with such X-ray powder analyses result from a variety of factors including: (a) errors in sample preparation (e.g., sample height); (b) instrument errors (e.g., flat sample errors); (c) calibration errors; (d) operator errors (including those errors present when determining the peak locations); and (e) the nature of the material (e.g., preferred orientation and transparency errors). Calibration errors and sample height errors often result in a shift of all the peaks in the same direction. Small differences in sample height when using a flat holder will lead to large displacements in PXRD peak positions. A systematic study showed that, using a Shimadzu XRD-6000 in the typical Bragg-Brentano configuration, sample height difference of 1 mm led to peak shifts as high as 1 degree (2θ (Chen et al., *J Pharmaceutical and Biomedical Analysis* 26:63 (2001)). These shifts can be identified from the X-ray diffractogram and can be eliminated by compensating for the shift (applying a systematic correction factor to all peak position values) or recalibrating the instrument. As mentioned above, it is possible to rectify measurements from the various machines by applying a systematic correction factor to bring the peak positions into agreement. In general, this correction factor will bring the measured peak positions from the Bruker into agreement with the expected peak positions and may be in the range of 0 to 0.2 degrees (2θ.

One of skill in the art will appreciate that the peak positions (2θ) will show some inter-apparatus variability, typically as much as 0.1 to 0.2 degrees (2θ. Accordingly, where peak positions (2θ) are reported, one of skill in the art will recognize that such numbers are intended to encompass such inter-apparatus variability. Furthermore, where the crystalline forms of the present invention are described as having a powder X-ray diffraction pattern essentially the same as that shown in a given figure, the term "essentially the same" is also intended to encompass such inter-apparatus variability in diffraction peak positions. Further, one skilled in the art will appreciate that relative peak intensities will show inter-apparatus variability as well as variability due to the degree of crystallinity, preferred orientation, prepared sample surface, and other factors known to those skilled in the art, and should be taken as qualitative measures only.

The different crystalline forms and amorphous form of the present invention can also be characterized using solid state NMR spectroscopy.

The $^{13}C$ solid state spectra can be collected as follows. Approximately 80 mg of sample were tightly packed into a 4 mm $ZrO_2$ spinner. The spectra were collected at ambient temperature and pressure on a 4 mm Bruker-Biospin CPMAS probe positioned into a wide-bore Bruker-Biospin Avance DSX 500 MHz NMR spectrometer. The sample was positioned at the magic angle and spun at 15.0 kHz. The fast spinning speed minimized the intensities of the spinning side bands. The $^{13}C$ solid state spectrum was collected using a proton decoupled cross-polarization magic angle spinning experiment (CPMAS). The cross-polarization contact time was set to 2.0 ms. A proton decoupling field of approximately 90 kHz was applied. The number of scans was adjusted to obtain adequate S/N. The recycle delay was adjusted approximately to 1.5 times the proton longitudinal relaxation time calculated based on proton detected proton inversion recovery relaxation experiment. The carbon spectrum was referenced using an external standard of crystalline adamantane, setting its upfield resonance to 29.5 ppm.

The $^{15}N$ solid state spectra can be collected as follows. Approximately 270 mg of sample were tightly packed into a 7 mm $ZrO_2$ spinner. The spectra were collected at ambient temperature and pressure on a 7 mm Bruker-Biospin CPMAS probe positioned into a wide-bore Bruker-Biospin Avance DSX 500 MHz NMR spectrometer. The sample was positioned at the magic angle and spun at 7.0 kHz. The fast spinning speed minimized the intensities of the spinning side bands. The $^{15}N$ solid state spectrum was collected using a proton decoupled cross-polarization magic angle spinning experiment (CPMAS). The cross-polarization contact time was set to 3.0 ms. A proton decoupling field of approximately 70 kHz was applied. The number of scans was adjusted to obtain adequate S/N. The recycle delay was adjusted approximately to 1.5 times the proton longitudinal relaxation time calculated based on proton detected proton inversion recovery relaxation experiment. The nitrogen spectrum was referenced using an external standard of crystalline D,L-alanine, setting its resonance to −331.5 ppm.

Crystalline forms can also be characterized using Raman spectroscopy. For example, Form XXV of Compound 1 was characterized using Raman spectroscopy as follows. The Raman spectra were collected using a ThermoNicolet 960 FT-Raman spectrometer equipped with a 1064 nm NdYAG laser and InGaAs detector. Samples were analyzed in NMR tubes. The spectra were collected using 1 W of laser power and 100 co-added scans. The collection range was 3700-100 $cm^{-1}$. Peaks were identified using the ThermoNicolet Omnic 6.0a software peak picking algorithm using a sensitivity setting of 70 and an intensity threshold of 0.4. All spectra were recorded using 4 $cm^{-1}$ resolution and Happ-Genzel apodization. Wavelength calibration was performed using polystyrene.

The solid forms of the present invention may also comprise more than one polymorphic form. One of skill in the art will also recognize that crystalline forms of a given compound can exist in substantially pure forms of a single polymorph, but can also exist in a crystalline form that comprises two or more different polymorphs or amorphous forms. Where a solid form comprises two or more polymorphs, the X-ray diffraction pattern will have peaks characteristic of each of the individual polymorphs of the present invention. For example, a solid form that comprises two polymorphs will have a powder X-ray diffraction pattern that is a convolution of the two X-ray diffraction patterns that correspond to the substantially pure polymorphic forms. For example, a solid form of Compound 1 can contain a first and second polymorphic form where the solid form contains at least 10% by weight of the first polymorph. In a further example, the solid form contains at least 20% by weight of the first polymorph. Even further examples contain at least 30%, at least 40%, or at least 50% by weight of the first polymorph. One of skill in the art will recognize that many such combinations of several individual polymorphs and amorphous forms in varying amounts are possible.

A. Polymorph Form XXV

Crystalline Form XXV of Compound 1 is an anhydrous crystalline form that can be produced as described in Example 1. Form XXV has several unexpected advantages over previously discovered crystalline forms of Compound 1. For example, although Form XLI described herein is the most thermodynamically stable crystalline form of Compound 1 under processing and storage conditions, Form XXV is more thermodynamically stable than previously discovered crystalline forms of Compound 1 (based on density, heat of fusion, and solubility). In addition, when compared to Form IV (previously identified as the most suitable polymorphic form of Compound 1 for a pharmaceutical formulation—see U.S. Application Publication No. 2006-0094763), Form XXV has improved photo stability, has a more regular crystalline shape, does not have a tendency to form agglomerates, has better bulk flow properties, and does not adhere to in-tank probes. Such improved properties are important for better tablet processing and manufacturing. Furthermore, during a recent manufacturing procedure, it took 26 hours to filter the Form IV batch, and only 4 hours to filter the Form XXV batch, which was of comparable size using the same filter/dryer equipment. Finally, the process for preparing Form XXV can utilize ethanol, whereas the process for preparing Form IV uses n-heptane. As will be appreciated by those of skill in the art, the use of ethanol instead of n-heptane can have several significant advantages, including: ethanol does not hold static charge similar to n-heptane (i.e. build-up of static charge is a safety concern due to potential for fire, therefore a special equipment configuration to improve grounding is needed when processing with heptane); processing with heptane can not be done in glass-lined vessels because of static dissipation issues; heptane has a flash point of −4° C. versus 13° C. for ethanol; heptane has an R50/53 risk phrase (indicating very toxic to aquatic organisms, and may cause long-term adverse effects in the aquatic environment) while ethanol does not contain this risk.

Crystalline Form XXV of Compound 1 was characterized by the PXRD pattern shown in FIG. 1. The PXRD pattern of Form XXV, expressed in terms of the degree (2θ) and relative intensities with a relative intensity of ≥2.0%, measured on a Bruker D5000 diffractometer with CuKα radiation, is also shown in Table 1.

TABLE 1

| Angle (Degree 2θ) | Relative Intensity* (≥2.0%) |
| --- | --- |
| 5.1 | 63.7 |
| 7.9 | 35.6 |
| 10.2 | 10.2 |
| 10.7 | 18.0 |
| 12.6 | 8.8 |
| 14.8 | 11.9 |
| 15.1 | 43.4 |
| 15.2 | 40.5 |
| 15.9 | 100.0 |
| 16.9 | 5.5 |
| 18.2 | 40.5 |
| 19.4 | 19.0 |
| 19.8 | 28.1 |
| 20.0 | 3.4 |
| 20.4 | 4.8 |
| 21.0 | 18.0 |
| 21.5 | 17.3 |
| 21.7 | 34.8 |
| 22.6 | 18.2 |
| 22.8 | 30.1 |
| 23.4 | 18.2 |
| 24.2 | 11.2 |
| 24.8 | 9.2 |
| 24.9 | 9.8 |
| 25.4 | 11.5 |
| 25.7 | 7.1 |
| 26.2 | 63.4 |
| 26.5 | 11.1 |
| 26.7 | 6.8 |
| 28.3 | 5.1 |
| 29.0 | 9.2 |
| 29.6 | 9.5 |
| 29.8 | 7.6 |
| 30.4 | 9.5 |
| 30.8 | 5.8 |
| 31.4 | 3.6 |
| 31.8 | 8.3 |
| 32.1 | 5.1 |
| 32.5 | 3.6 |
| 33.1 | 7.3 |
| 33.9 | 3.7 |
| 34.3 | 7.4 |
| 34.8 | 3.5 |
| 35.5 | 3.4 |
| 36.1 | 5.7 |
| 36.9 | 8.4 |
| 37.3 | 4.0 |
| 37.7 | 3.0 |

TABLE 1-continued

| Angle (Degree 2θ) | Relative Intensity* (≥2.0%) |
|---|---|
| 38.5 | 6.5 |
| 38.6 | 6.3 |
| 39.1 | 2.8 |
| 39.6 | 2.3 |

*The relative intensities may change depending on the crystal size and morphology.

Figure 2:
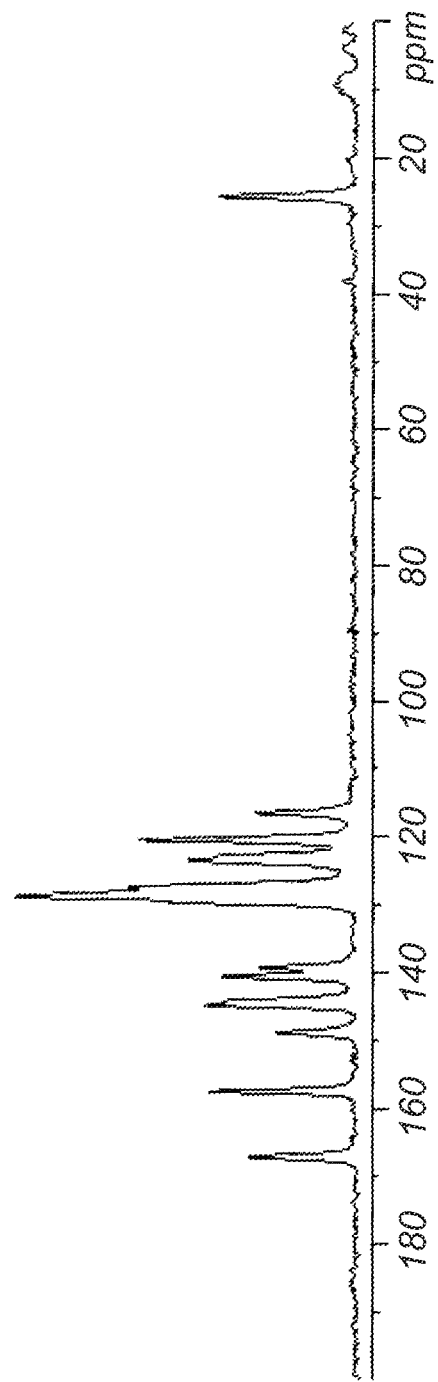
FIG. 2 shows a $^{13}$C solid state NMR spectrum of Compound 1 Form XXV carried out on a Bruker-Biospin 4 mm BL triple resonance CPMAS probe positioned into a wide-bore Bruker-Biospin Avance DSX 500 MHz NMR spectrometer.

Crystalline Form XXV of Compound 1 was also characterized by the solid state NMR spectral pattern shown in FIG. 2, carried out on a Bruker-Biospin 4 mm BL CPMAS probe positioned into a wide-bore Bruker-Biospin Avance DSX 500 MHz NMR spectrometer. The $^{13}$C chemical shifts of Form XXV of Compound 1 are shown in Table 2.

TABLE 2

| $^{13}$C Chemical Shifts$^a$ [ppm] | Intensity$^b$ |
|---|---|
| 167.4 | 3.7 |
| 157.7 | 5.1 |
| 149.1 | 2.7 |
| 145.0 | 5.2 |
| 144.4 | 4.6 |
| 140.7 | 4.6 |
| 139.4 | 3.3 |
| 129.7 | 6.5 |
| 128.8 | 12.0 |
| 127.4 | 8.0 |
| 123.5 | 5.8 |
| 120.5 | 7.6 |
| 116.6 | 3.4 |
| 25.6 | 4.7 |

$^a$Referenced to external sample of solid phase adamantane at 29.5 ppm.
$^b$Defined as peak heights. Intensities can vary depending on the actual setup of the CPMAS experimental parameters and the thermal history of the sample. CPMAS intensities are not necessarily quantitative.

Figure 3:
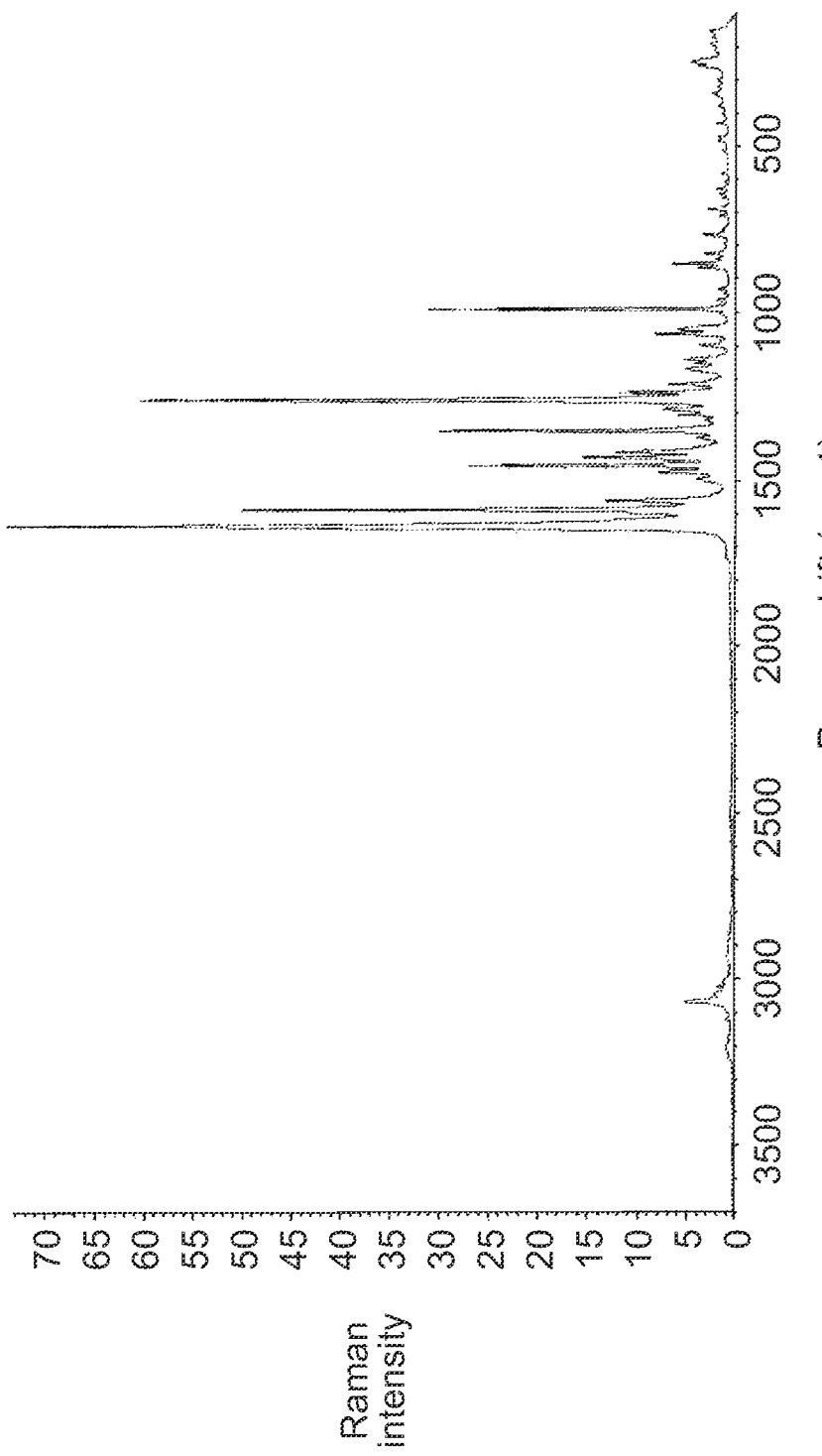
FIG. 3 shows a Raman spectrum of Compound 1 Form XXV carried out on a ThermoNicolet 960 FT-Raman spectrometer equipped with a 1064 nm NdYAG laser and InGaAs detector.

Crystalline Form XXV of Compound 1 was also characterized by the following Raman spectral pattern, provided in FIG. 3, carried out on a ThermoNicolet 960 FT-Raman Spectrometer equipped with a 1064 nm NdYAG laser and InGaAs detector. The Raman spectral peaks of Form XXV of Compound 1 are shown in Table 3.

TABLE 3

| Wavenumber (cm$^{-1}$) |
|---|
| 3068 |
| 1637 |
| 1587 |
| 1560 |
| 1496 |
| 1476 |
| 1456 |
| 1431 |
| 1416 |
| 1373 |
| 1351 |
| 1303 |
| 1288 |
| 1260 |
| 1238 |
| 1213 |
| 1166 |
| 1150 |
| 1138 |
| 1098 |
| 1064 |
| 990 |
| 962 |
| 928 |
| 866 |
| 853 |
| 822 |
| 766 |
| 690 |
| 474 |
| 244 |

B. Polymorph Form XVI

Crystalline Form XVI of Compound 1 is a solvate form that can be produced as described in Example 1.

Figure 4:
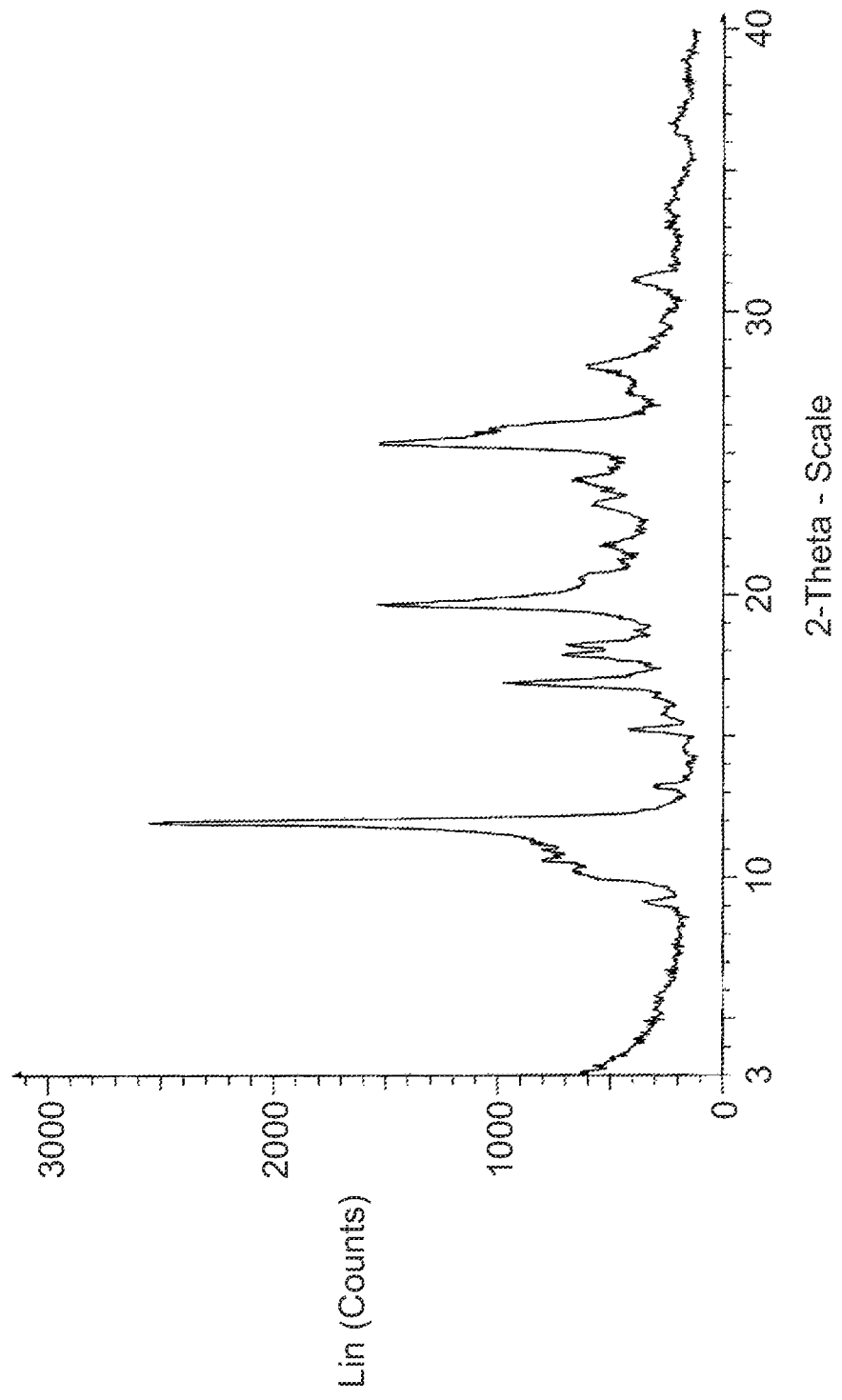
FIG. 4 shows a PXRD pattern of Compound 1 Form XVI carried out on a Bruker D5000 diffractometer.

Crystalline Form XVI of Compound 1 was characterized by the PXRD pattern shown in FIG. 4. The PXRD pattern of Form XVI, expressed in terms of the degree (2θ) and relative intensities with a relative intensity of ≥6.0%, measured on a Bruker D5000 diffractometer with CuKα radiation, is also shown in Table 4.

TABLE 4

| Angle (Degree 2θ) | Relative Intensity* (≥6.0%) |
|---|---|
| 5.8 | 11.7 |
| 9.1 | 13.7 |
| 10.2 | 26.0 |
| 10.6 | 31.3 |
| 11.9 | 100.0 |
| 13.2 | 11.9 |
| 14.4 | 6.7 |
| 15.2 | 16.2 |
| 15.7 | 10.6 |
| 16.8 | 38.0 |
| 17.9 | 27.9 |
| 18.2 | 27.0 |
| 19.7 | 60.3 |
| 20.6 | 24.9 |
| 21.2 | 17.7 |
| 21.7 | 21.4 |
| 23.2 | 22.5 |
| 24.1 | 26.3 |
| 25.4 | 60.0 |
| 25.9 | 40.6 |
| 27.2 | 16.5 |
| 28.0 | 23.4 |
| 29.0 | 12.7 |
| 29.8 | 10.4 |
| 31.1 | 16.5 |

*The relative intensities may change depending on the crystal size and morphology.

C. Polymorph Form VIII

Crystalline Form VIII of Compound 1 is a solvate form that can be produced as described in Example 1. Form VIII can also be produced as described in U.S. Application Publication No. 2006-0094763.

Figure 5:
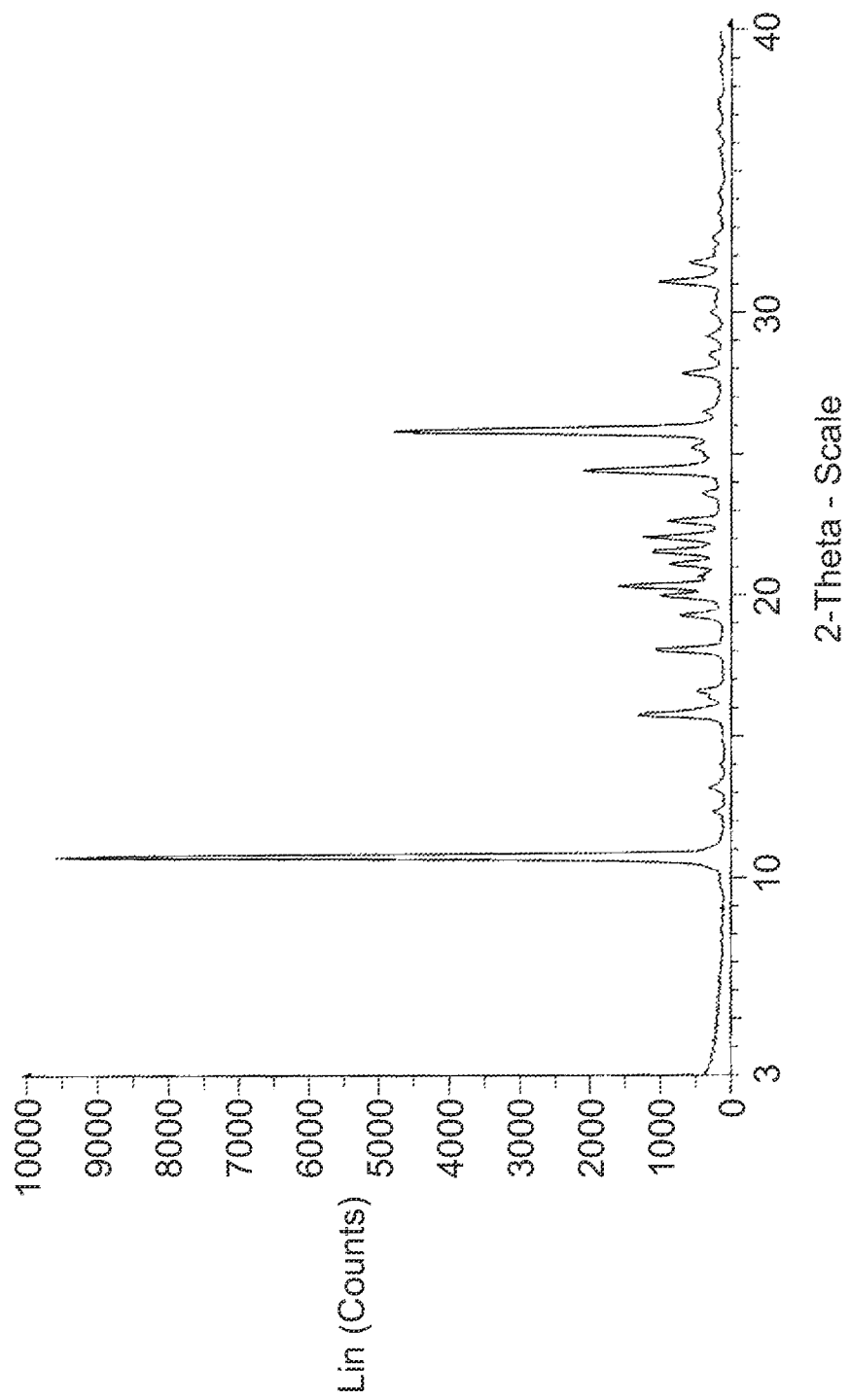
FIG. 5 shows a PXRD pattern of Compound 1 Form VIII carried out on a Bruker D5000 diffractometer.

Crystalline Form VIII of Compound 1 was characterized by the PXRD pattern shown in FIG. 5. The PXRD pattern of Form VIII, expressed in terms of the degree (2θ) and relative intensities with a relative intensity of ≥2.0%, measured on a Bruker D5000 diffractometer with CuKα radiation, is also shown in Table 5.

TABLE 5

| Angle (Degree 2θ) | Relative Intensity* (≥2.0%) |
|---|---|
| 10.7 | 100.0 |
| 12.3 | 2.4 |
| 13.2 | 3.0 |

TABLE 5-continued

| Angle (Degree 2θ) | Relative Intensity* (≥2.0%) |
|---|---|
| 15.7 | 13.4 |
| 16.3 | 3.2 |
| 16.6 | 4.8 |
| 18.0 | 10.8 |
| 19.3 | 7.3 |
| 20.0 | 10.2 |
| 20.3 | 16.3 |
| 20.7 | 4.7 |
| 21.1 | 8.9 |
| 21.6 | 11.3 |
| 22.0 | 12.7 |
| 22.6 | 9.2 |
| 23.6 | 4.0 |
| 24.4 | 21.7 |
| 25.2 | 5.6 |
| 25.8 | 49.8 |
| 26.5 | 4.1 |
| 27.9 | 7.0 |
| 28.5 | 3.1 |
| 29.2 | 3.5 |
| 30.0 | 2.9 |
| 31.1 | 10.4 |
| 31.8 | 5.9 |
| 32.7 | 2.7 |

*The relative intensities may change depending on the crystal size and morphology.

D. Polymorph Form XLI

Crystalline Form XLI of Compound 1 is an anhydrous crystalline form that can be produced as described in Example 1. Form XLI has several unexpected advantages over previously discovered crystalline forms of Compound 1. For example, Form XLI is the most thermodynamically stable polymorphic form (based on density, heat of fusion, and solubility) known of Compound 1. In addition, when compared to Form IV (previously identified as the most suitable polymorphic form of Compound 1 for a pharmaceutical formulation—see U.S. Application Publication No. 2006-0094763), Form XLI has improved photo stability, has a more regular crystalline shape, does not have a tendency to form agglomerates, has better bulk flow properties, and does not adhere to in-tank probes. Such improved properties are important for better tablet processing and manufacturing. Since Form XLI has a more regular crystalline shape and forms larger crystals than Form IV, the filtration rate and cake wash rate are improved for Form XLI compared to Form IV. Finally, the process for preparing Form XLI can utilize ethanol, whereas the process for preparing Form IV uses n-heptane. As will be appreciated by those of skill in the art, the use of ethanol instead of n-heptane can have several significant advantages, including: ethanol does not hold static charge similar to n-heptane (i.e. build-up of static charge is a safety concern due to potential for fire, therefore a special equipment configuration to improve grounding is needed when processing with heptane); processing with heptane can not be done in glass-lined vessels because of static dissipation issues; heptane has a flash point of −4° C. versus 13° C. for ethanol; heptane has an R50/53 risk phrase (indicating very toxic to aquatic organisms, and may cause long-term adverse effects in the aquatic environment) while ethanol does not contain this risk.

Figure 6:
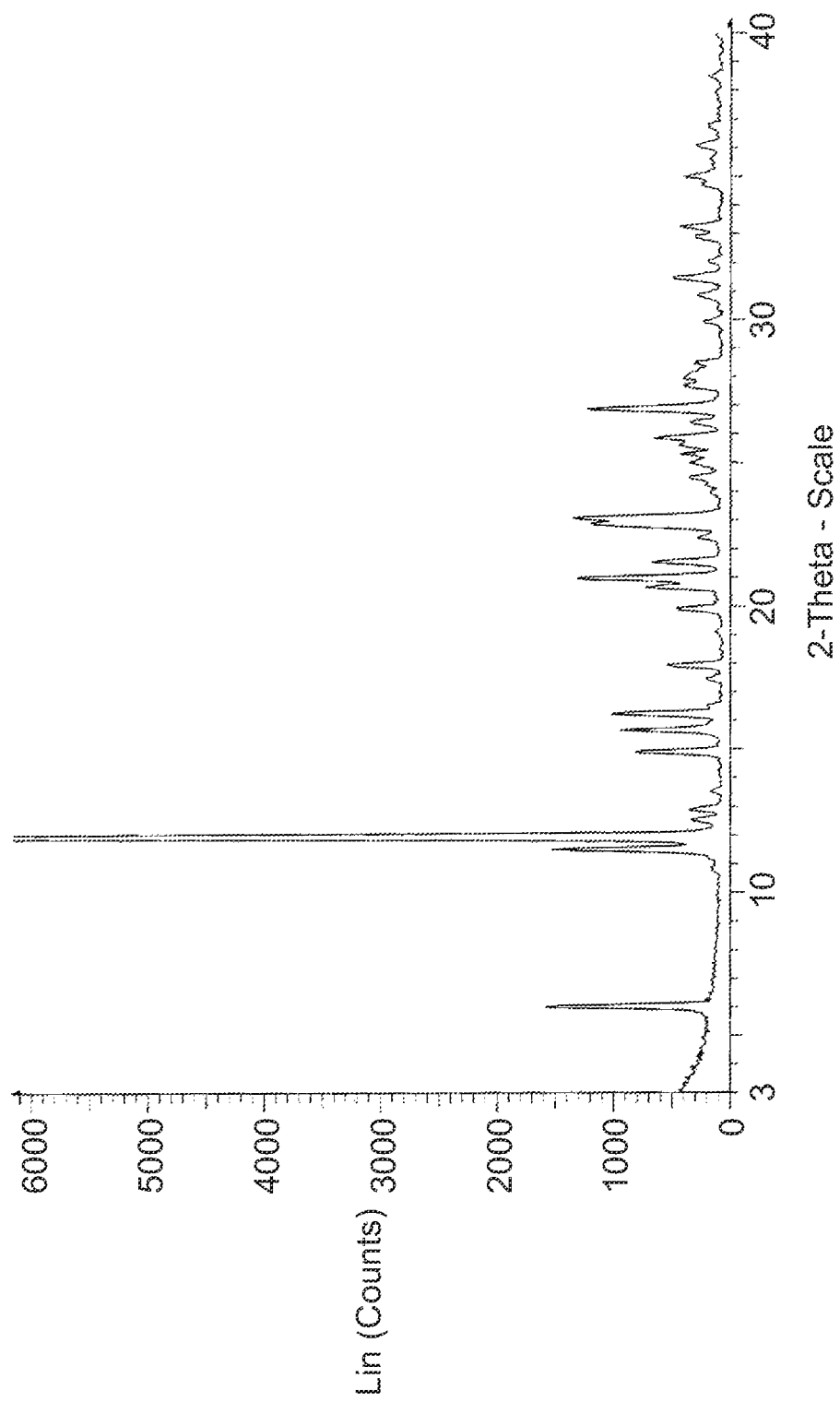
FIG. 6 shows a PXRD pattern of Compound 1 Form XLI carried out on a Bruker D5000 diffractometer.

Crystalline Form XLI of Compound 1 was characterized by the PXRD pattern shown in FIG. 6. The PXRD pattern of Form XLI, expressed in terms of the degree (2θ) and relative intensities with a relative intensity of ≥2.0%, measured on a Bruker D5000 diffractometer with CuKα radiation, is also shown in Table 6.

TABLE 6

| Angle (Degree 2θ) | Relative Intensity* (≥2.0%) |
|---|---|
| 6.0 | 15.1 |
| 11.5 | 14.6 |
| 11.9 | 100.0 |
| 12.5 | 3.1 |
| 12.9 | 3.3 |
| 14.9 | 7.7 |
| 15.6 | 8.9 |
| 16.2 | 9.7 |
| 16.5 | 3.6 |
| 17.9 | 5.1 |
| 19.9 | 4.3 |
| 20.7 | 6.8 |
| 21.0 | 12.5 |
| 21.6 | 6.3 |
| 22.4 | 2.6 |
| 22.8 | 11.4 |
| 23.1 | 12.8 |
| 24.2 | 2.6 |
| 24.5 | 3.2 |
| 25.0 | 3.2 |
| 25.3 | 3.9 |
| 25.6 | 4.1 |
| 25.9 | 6.1 |
| 26.4 | 3.2 |
| 26.9 | 11.7 |
| 27.7 | 3.7 |
| 28.0 | 3.7 |
| 28.1 | 3.9 |
| 28.5 | 2.8 |
| 29.9 | 2.1 |
| 30.9 | 2.6 |
| 31.5 | 4.6 |
| 32.9 | 2.7 |
| 33.2 | 4.0 |
| 34.8 | 2.3 |
| 35.0 | 3.7 |
| 36.1 | 2.7 |

*The relative intensities may change depending on the crystal size and morphology.

Figure 7:
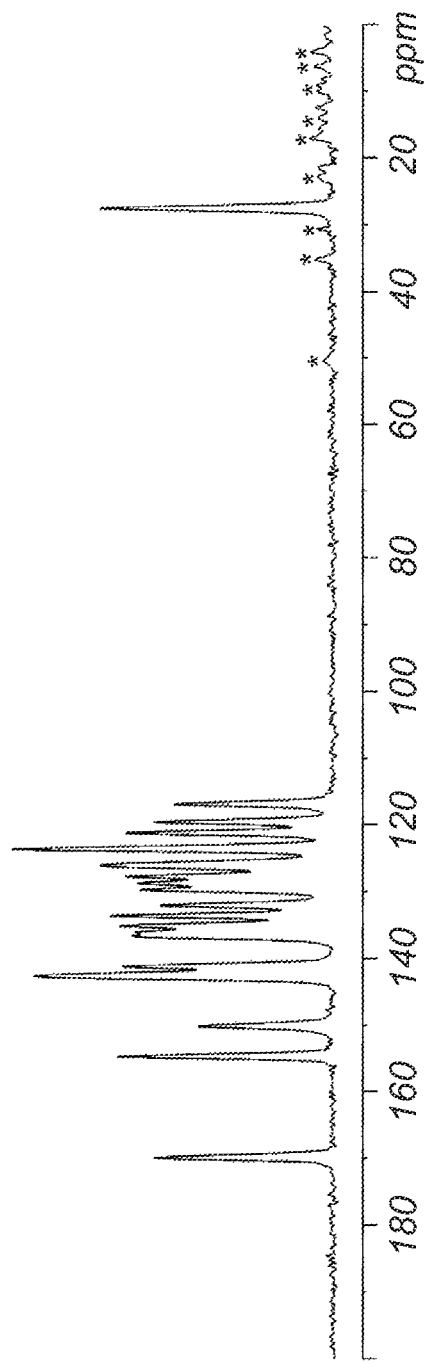
FIG. 7 shows a $^{13}$C solid state NMR spectrum of Compound 1 Form XLI carried out on a Bruker-Biospin 4 mm BL triple resonance CPMAS probe positioned into a wide-bore Bruker-Biospin Avance DSX 500 MHz NMR spectrometer.

Crystalline Form XLI of Compound 1 was also characterized by the solid state NMR spectral pattern shown in FIG. 7, carried out on a Bruker-Biospin 4 mm BL CPMAS probe positioned into a wide-bore Bruker-Biospin Avance DSX 500 MHz NMR spectrometer. The $^{13}C$ chemical shifts of Form XLI of Compound 1 are shown in Table 7.

TABLE 7

| $^{13}C$ Chemical Shifts[a] [ppm] | Intensity[b] |
|---|---|
| 169.9 | 6.56 |
| 154.6 | 7.94 |
| 150.1 | 4.87 |
| 142.4 | 11.18 |
| 141.1 | 7.74 |
| 136.6 | 7.39 |
| 136.0 | 7.27 |
| 135.0 | 7.88 |
| 133.5 | 8.23 |
| 132.0 | 6.34 |
| 129.6 | 7.09 |
| 128.7 | 7.17 |
| 127.7 | 7.64 |
| 126.0 | 8.6 |
| 123.5 | 12 |
| 121.2 | 7.63 |
| 119.6 | 6.53 |
| 116.9 | 5.78 |
| 27.5 | 8.63 |

[a] Referenced to external sample of solid phase adamantane at 29.5 ppm.
[b] Defined as peak heights. Intensities can vary depending on the actual setup of the CPMAS experimental parameters and the thermal history of the sample. CPMAS intensities are not necessarily quantitative.

Figure 8:
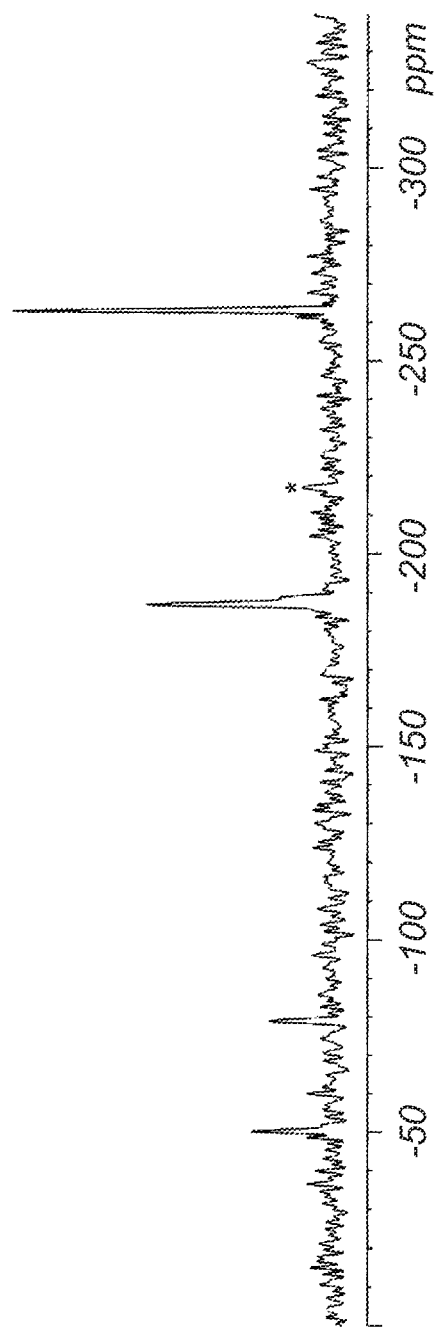
FIG. 8 shows a $^{15}$N solid state NMR spectrum of Compound 1 Form XLI carried out on a Bruker-Biospin 4 mm BL triple resonance CPMAS probe positioned into a wide-bore Bruker-Biospin Avance DSX 500 MHz NMR spectrometer.

Crystalline Form XLI of Compound 1 was also characterized by the solid state NMR spectral pattern shown in FIG. 8, carried out on a Bruker-Biospin 4 mm BL CPMAS probe positioned into a wide-bore Bruker-Biospin Avance DSX 500 MHz NMR spectrometer. The $^{15}$N chemical shifts of Form XLI of Compound 1 are shown in Table 8.

TABLE 8

| $^{15}$N Chemical Shifts[a] [ppm] | Intensity[b] |
|---|---|
| −50.2 | 2.96 |
| −79.0 | 2.34 |
| −187.1 | 6.98 |
| −263.2 | 12 |

[a]Referenced to external sample of solid phase D,L-alanine at −331.5 ppm.
[b]Defined as peak heights. Intensities can vary depending on the actual setup of the CPMAS experimental parameters and the thermal history of the sample. CPMAS intensities are not necessarily quantitative.

Figure 9:
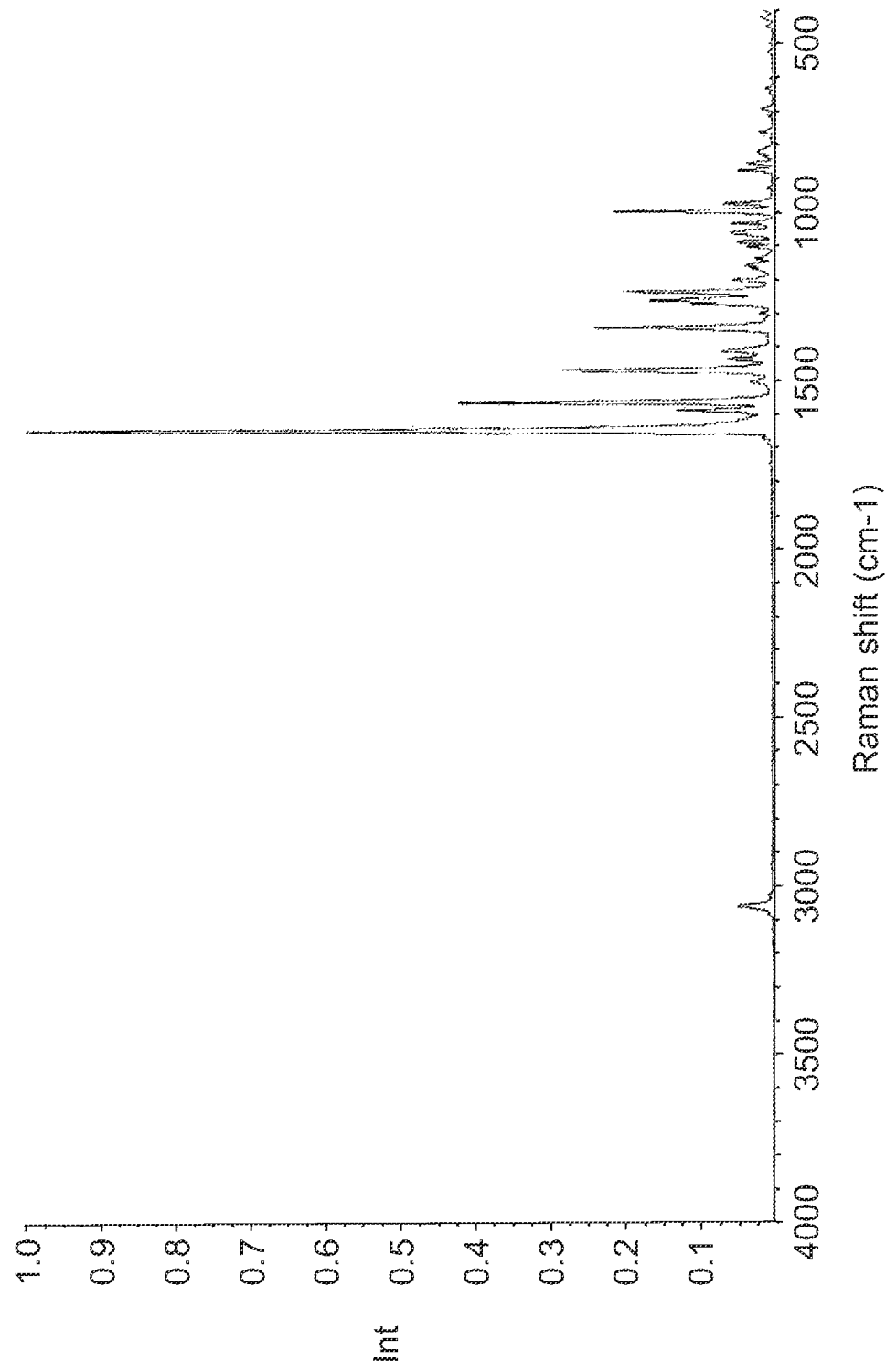
FIG. 9 shows a Raman spectrum of Compound 1 Form XLI carried out on a ThermoNicolet 960 FT-Raman spectrometer equipped with a 1064 nm NdYAG laser and InGaAs detector.

Crystalline Form XLI of Compound 1 was also characterized by the following Raman spectral pattern, provided in FIG. 9, carried out on a ThermoNicolet 960 FT-Raman Spectrometer equipped with a 1064 nm NdYAG laser and InGaAs detector. The Raman spectral peaks of Form XLI of Compound 1 are shown in Table 9.

TABLE 9

| Wavenumber (cm$^{-1}$) |
|---|
| 3084 |
| 3060 |
| 3029 |
| 2934 |
| 1671 |
| 1648 |
| 1589 |
| 1564 |
| 1503 |
| 1468 |
| 1434 |
| 1411 |
| 1341 |
| 1299 |
| 1271 |
| 1261 |
| 1235 |
| 1199 |
| 1166 |
| 1157 |
| 1136 |
| 1101 |
| 995 |
| 973 |
| 928 |
| 875 |
| 854 |
| 835 |
| 821 |
| 761 |
| 715 |
| 693 |
| 646 |
| 631 |
| 525 |
| 448 |
| 420 |
| 400 |
| 359 |
| 315 |
| 276 |
| 245 |
| 224 |
| 184 |
| 149 |

E. Polymorph Form IX

Crystalline Form IX of Compound 1 is a hydrate crystalline form that can be produced as described in Example 2. Crystalline Form IX of Compound 1 is a preferred form for development of aqueous-based pharmaceutical formulations. Crystalline Form IX of Compound 1 is more stable than Form IV in aqueous-based pharmaceutical formulations, since, as shown in Example 2, Form IV may convert to Form IX in an aqueous environment. Hydrates typically have lower solubility in water versus anhydrous forms. This may be advantageous in the development of controlled or sustained-release pharmaceutical preparations.

Figure 10:
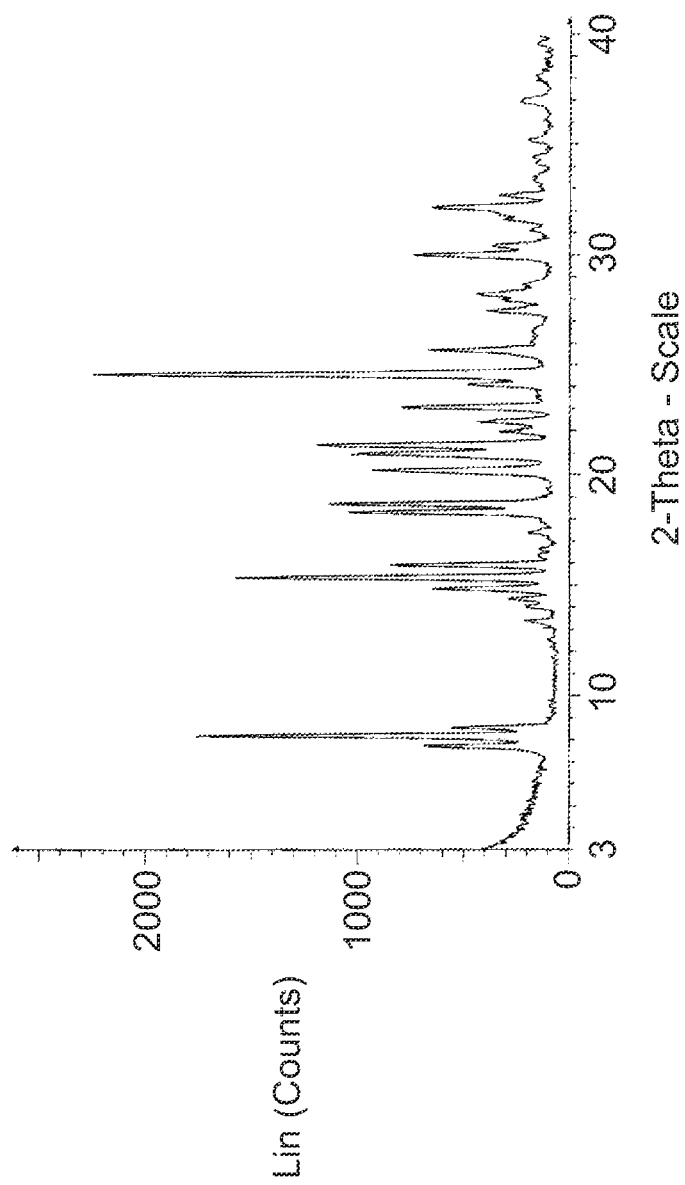
FIG. 10 shows a PXRD pattern of Compound 1 Form IX carried out on a Bruker D5000 diffractometer.

Crystalline Form IX of Compound 1 was characterized by the PXRD pattern shown in FIG. 10. The PXRD pattern of Form IX, expressed in terms of the degree (2θ) and relative intensities with a relative intensity of ≥2.0%, measured on a Bruker D5000 diffractometer with CuKα radiation, is also shown in Table 10.

TABLE 10

| Angle (Degree 2θ) | Relative Intensity* (≥2.0%) |
|---|---|
| 7.7 | 30.5 |
| 8.1 | 78.1 |
| 8.5 | 24.7 |
| 12.5 | 4.5 |
| 13.0 | 7.1 |
| 13.4 | 9.3 |
| 14.0 | 9.0 |
| 14.4 | 12.8 |
| 14.8 | 28.7 |
| 15.3 | 69.9 |
| 15.9 | 37.6 |
| 16.3 | 6.6 |
| 16.6 | 6.3 |
| 17.3 | 8.7 |
| 18.3 | 46.6 |
| 18.7 | 50.3 |
| 20.2 | 41.4 |
| 21.0 | 46.1 |
| 21.3 | 53.0 |
| 21.9 | 14.5 |
| 22.4 | 19.8 |
| 23.1 | 35.4 |
| 24.1 | 21.4 |
| 24.6 | 100.0 |
| 25.7 | 29.6 |
| 26.1 | 9.0 |
| 26.5 | 8.5 |
| 27.5 | 17.3 |
| 28.0 | 14.2 |
| 28.2 | 19.4 |
| 28.6 | 9.9 |
| 30.0 | 33.0 |
| 30.4 | 16.3 |
| 31.2 | 7.8 |
| 31.6 | 13.9 |
| 32.2 | 28.9 |
| 32.7 | 14.8 |
| 33.4 | 7.9 |
| 34.2 | 7.2 |
| 34.5 | 7.2 |
| 35.2 | 8.7 |
| 37.0 | 10.3 |
| 38.0 | 6.6 |
| 39.6 | 6.7 |
| 39.3 | 3.9 |

*The relative intensities may change depending on the crystal size and morphology.

Figure 11:
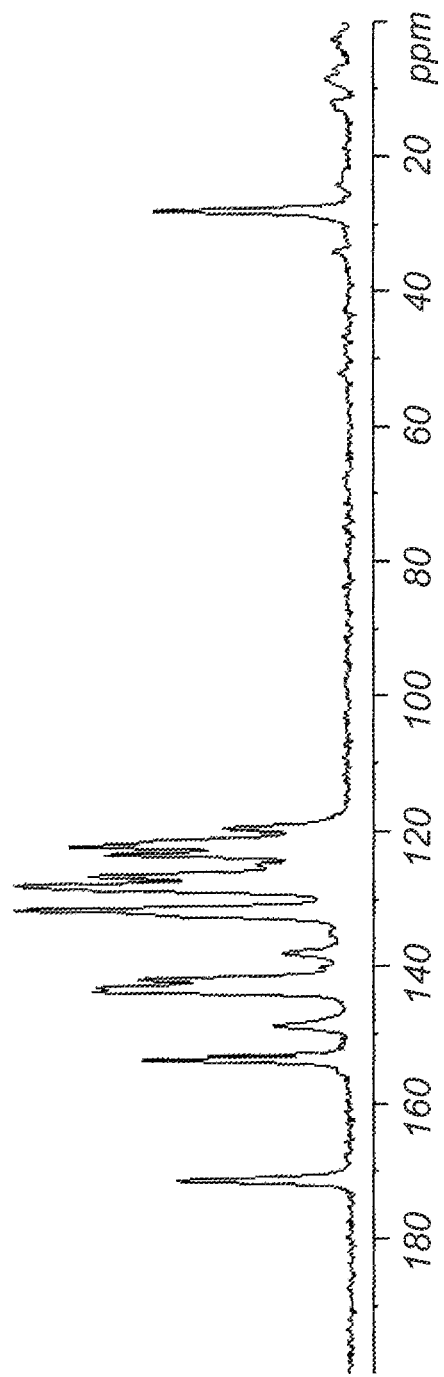
FIG. 11 shows a $^{13}$C solid state NMR spectrum of Compound 1 Form IX carried out on a Bruker-Biospin 4 mm BL triple resonance CPMAS probe positioned into a wide-bore Bruker-Biospin Avance DSX 500 MHz NMR spectrometer.

Crystalline Form IX of Compound 1 was also characterized by the solid state NMR spectral pattern shown in FIG. 11, carried out on a Bruker-Biospin 4 mm BL CPMAS probe positioned into a wide-bore Bruker-Biospin Avance DSX 500 MHz NMR spectrometer. The $^{13}$C chemical shifts of Form IX of Compound 1 are shown in Table 11.

TABLE 11

| $^{13}$C Chemical Shifts$^a$ [ppm] | Intensity$^b$ |
|---|---|
| 171.4 | 6.1 |
| 153.6 | 7.4 |
| 148.8 | 2.5 |
| 143.6 | 9.1 |
| 143.0 | 9.0 |
| 141.9 | 7.5 |
| 138.1 | 2.2 |
| 131.5 | 12 |
| 127.9 | 12 |
| 126.5 | 9.2 |
| 124.9 | 3.1 |
| 123.4 | 8.7 |
| 122.1 | 10.0 |
| 119.5 | 4.3 |
| 28.0 | 6.9 |

(c) Referenced to external sample of solid phase adamantane at 29.5 ppm.
(d) Defined as peak heights. Intensities can vary depending on the actual setup of the CPMAS experimental parameters and the thermal history of the sample. CPMAS intensities are not necessarily quantitative.

E. Polymorph Form XII

Crystalline Form XII of Compound 1 is an ethanol solvate crystalline form that can be produced as described in Example 3.

Figure 12:
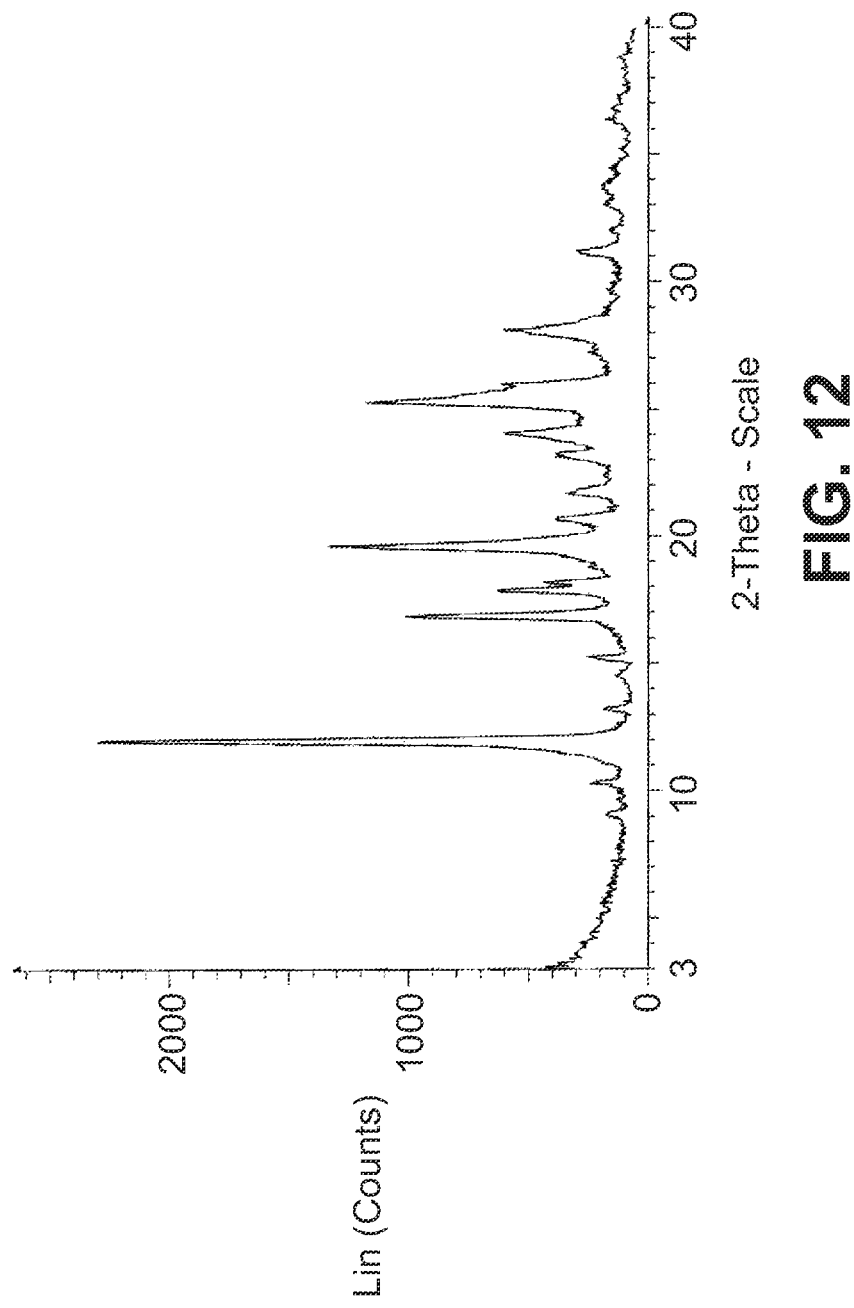
FIG. 12 shows a PXRD pattern of Compound 1 Form XII carried out on a Bruker D5000 diffractometer.

Crystalline Form XII of Compound 1 was characterized by the PXRD pattern shown in FIG. 12. The PXRD pattern of Form IX, expressed in terms of the degree (2θ) and relative intensities with a relative intensity of ≥2.0%, measured on a Bruker D5000 diffractometer with CuKα radiation, is also shown in Table 12.

TABLE 12

| Angle (Degree 2θ) | Relative Intensity* (≥2.0%) |
|---|---|
| 9.1 | 7.4 |
| 9.6 | 5.5 |
| 10.3 | 9.2 |
| 11.9 | 100 |
| 13.2 | 7.9 |
| 14.5 | 5.7 |
| 16.8 | 43.8 |
| 17.8 | 27.2 |
| 18.1 | 18.7 |
| 19.6 | 57.7 |
| 20.7 | 16.4 |
| 21.7 | 14.7 |
| 23.2 | 16.5 |
| 24.0 | 25.9 |
| 25.3 | 51.3 |
| 25.9 | 26.4 |
| 28.1 | 25.9 |
| 29.7 | 7.1 |
| 31.2 | 12.9 |
| 32.0 | 6.8 |
| 33.1 | 8 |
| 33.7 | 8.3 |
| 34.5 | 6.9 |
| 36.4 | 7.7 |
| 36.9 | 6.5 |
| 37.3 | 5.5 |
| 38.9 | 5.3 |
| 39.3 | 3.9 |

*The relative intensities may change depending on the crystal size and morphology.

F. Polymorph Form XV

Crystalline Form XV of Compound 1 is an ethanol solvate crystalline form that can be produced as described in Example 4.

Figure 13:
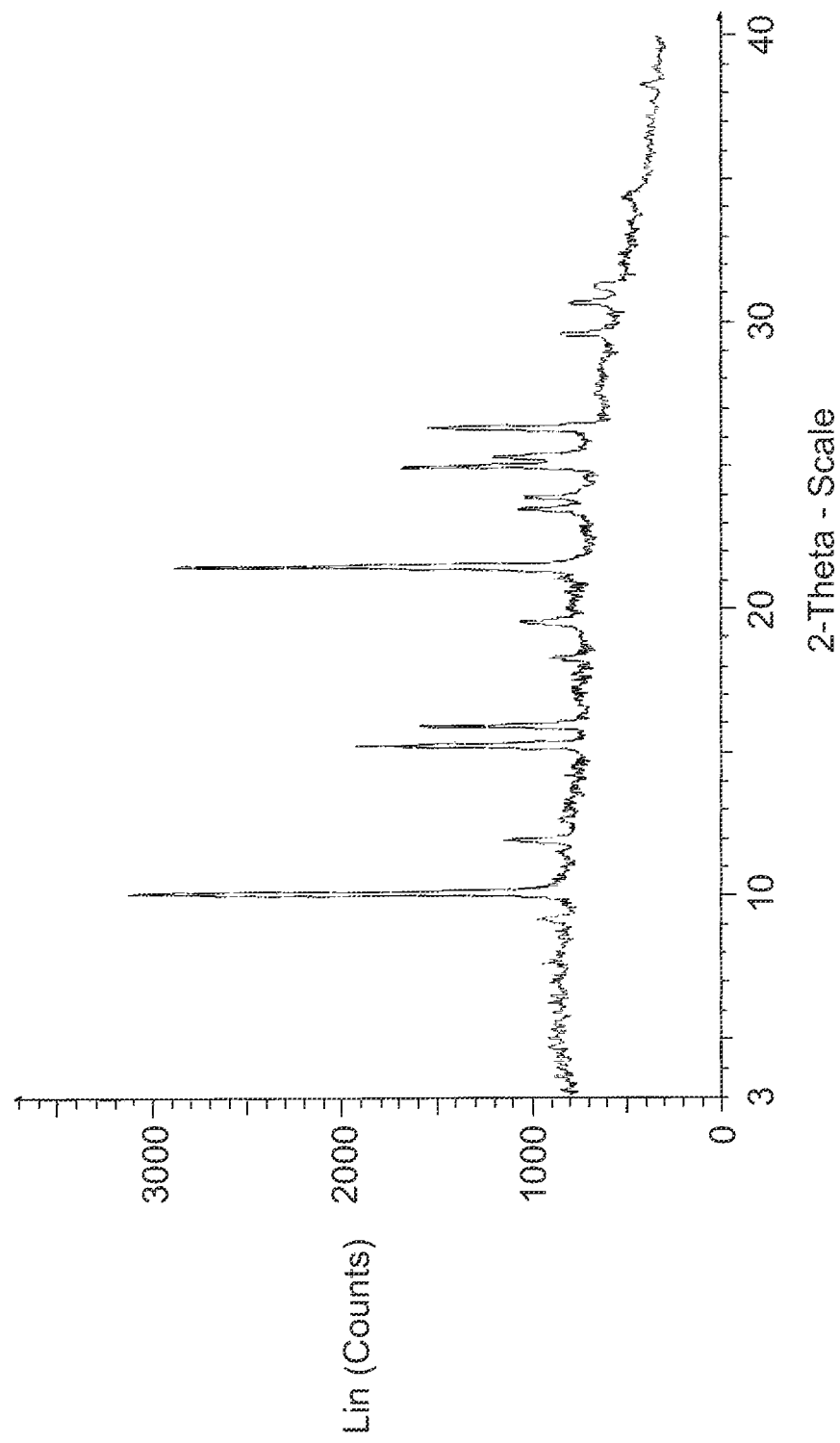
FIG. 13 shows a PXRD pattern of Compound 1 Form XV carried out on a Bruker D5000 diffractometer.

Crystalline Form XV of Compound 1 was characterized by the PXRD pattern shown in FIG. 13. The PXRD pattern of Form XV, expressed in terms of the degree (2θ) and relative intensities with a relative intensity of ≥2.0%, measured on a Bruker D5000 diffractometer with CuKα radiation, is also shown in Table 14.

TABLE 14

| Angle (Degree 2θ) | Relative Intensity* (≥2.0%) |
|---|---|
| 5.3 | 30.7 |
| 7.6 | 32.8 |
| 9.2 | 31.5 |
| 10.1 | 100.0 |
| 10.7 | 32.8 |
| 11.9 | 36.5 |
| 12.6 | 27.5 |
| 15.2 | 61.3 |
| 15.9 | 50.8 |
| 16.8 | 29.6 |
| 17.7 | 24.9 |
| 18.3 | 29.1 |
| 19.5 | 33.9 |
| 20.1 | 36.5 |
| 21.1 | 27.8 |
| 21.5 | 91.9 |
| 23.9 | 32.8 |
| 25.0 | 53.8 |
| 25.3 | 38.2 |
| 26.3 | 49.4 |
| 29.6 | 27.1 |
| 30.7 | 25.3 |
| 31.3 | 21.1 |
| 33.5 | 15.8 |
| 34.4 | 16.7 |

*The relative intensities may change depending on the crystal size and morphology.

G. Amorphous Form

An amorphous form of Compound 1 can be produced as described in Example 5. An amorphous form can also be produced as described in WIPO International Publication No. WO 2006/123223.

Figure 14:
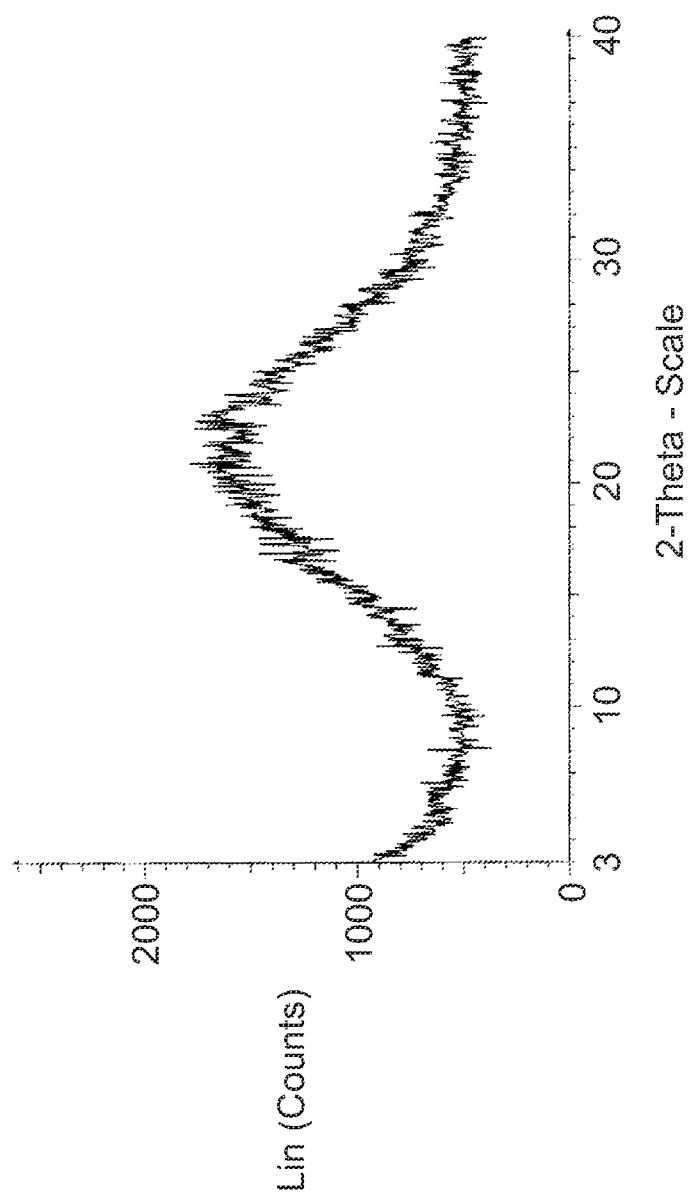
FIG. 14 shows a PXRD pattern of amorphous form of Compound 1 carried out on a Bruker D5000 diffractometer.
Figure 15:
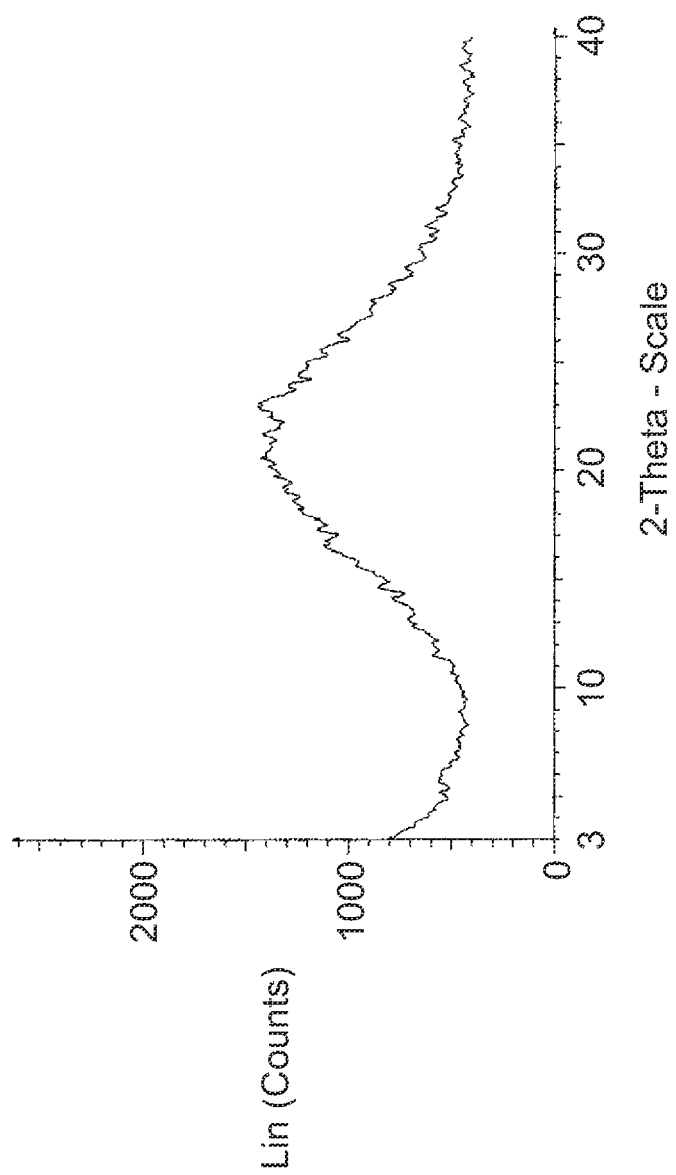
FIG. 15 shows a PXRD pattern of amorphous form of Compound 1 carried out on a Bruker D5000 diffractometer. The pattern is the same as in FIG. 14 except it was processed with a polynomial smoothing function to enhance detail.

The amorphous form of Compound 1 was characterized by the PXRD pattern shown in FIGS. 14 and 15, measured on a Bruker D5000 diffractometer with CuKα radiation.

Figure 16:
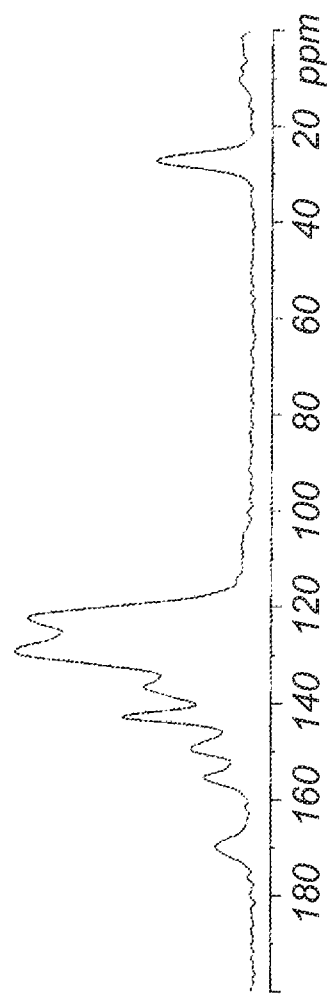
FIG. 16 shows a $^{13}$C solid state NMR spectrum of amorphous form of Compound 1 carried out on a Bruker-Biospin 4 mm BL triple resonance CPMAS probe positioned into a wide-bore Bruker-Biospin Avance DSX 500 MHz NMR spectrometer.

The amorphous form of Compound 1 was also characterized by the solid state NMR spectral pattern shown in FIG. 16, carried out on a Bruker-Biospin 4 mm BL CPMAS probe positioned into a wide-bore Bruker-Biospin Avance DSX 500 MHz NMR spectrometer. The $^{13}$C chemical shifts of an amorphous form of Compound 1 are shown in Table 15.

TABLE 15

| $^{13}$C Chemical Shifts$^a$ [ppm] | Intensity$^b$ |
|---|---|
| 169.9 | 1.43 |
| 155.4 | 2.05 |
| 149.6 | 2.74 |
| 142.8 | 6.36 |
| 136.6 | 5.21 |
| 129.1 | 12 |
| 122.2 | 11.34 |
| 27.3 | 4.62 |

(e) Referenced to external sample of solid phase adamantane at 29.5 ppm.
(f) Defined as peak heights. Intensities can vary depending on the actual setup of the CPMAS experimental parameters and the thermal history of the sample. CPMAS intensities are not necessarily quantitative.

II. Pharmaceutical Compositions of the Invention

The active agents (i.e., the polymorphs, or solid forms comprising two or more such polymorphs, of Compound 1 described herein or in U.S. Application No. 2006-0094763) of the invention may be formulated into pharmaceutical compositions suitable for mammalian medical use. Any suitable route of administration may be employed for providing a patient with an effective dosage of any of the polymorphic forms of Compound 1. For example, peroral or parenteral formulations and the like may be employed. Dosage forms include capsules, tablets, dispersions, suspensions and the like, e.g. enteric-coated capsules and/or tablets, capsules and/or tablets containing enteric-coated pellets of Compound 1. In all dosage forms, polymorphic forms of Compound 1 can be admixtured with other suitable constituents. The compositions may be conveniently presented in unit dosage forms, and prepared by any methods known in the pharmaceutical arts. Pharmaceutical compositions of the invention comprise a therapeutically effective amount of the active agent and one or more inert, pharmaceutically acceptable carriers, and optionally any other therapeutic ingredients, stabilizers, or the like. The carrier(s) must be pharmaceutically acceptable in the sense of being compatible with the other ingredients of the formulation and not unduly deleterious to the recipient thereof. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80", and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions according to the invention are listed in *Remington: The Science & Practice of Pharmacy,* 19$^{th}$ ed., Williams & Williams, (1995), and in the "Physician's Desk Reference", 52$^{nd}$ ed., Medical Economics, Montvale, N.J. (1998), and in *Handbook of Pharmaceutical Excipients,* 3$^{rd}$. Ed., Ed. A. H. Kibbe, Pharmaceutical Press, 2000. The active agents of the invention may be formulated in compositions including those suitable for oral, rectal, topical, nasal, ophthalmic, or parenteral (including intraperitoneal, intravenous, subcutaneous, or intramuscular injection) administration.

The amount of the active agent in the formulation will vary depending upon a variety of factors, including dosage form, the condition to be treated, target patient population, and other considerations, and will generally be readily determined by one skilled in the art. A therapeutically effective amount will be an amount necessary to modulate, regulate, or inhibit a protein kinase. In practice, this will vary widely depending upon the particular active agent, the severity of the condition to be treated, the patient population, the stability of the formulation, and the like. Compositions will generally contain anywhere from about 0.001% by weight to about 99% by weight active agent, preferably from about 0.01% to about 5% by weight active agent, and more preferably from about 0.01% to 2% by weight active agent, and will also depend upon the relative amounts of excipients/additives contained in the composition.

A pharmaceutical composition of the invention is administered in conventional dosage form prepared by combining a therapeutically effective amount of an active agent as an active ingredient with one or more appropriate pharmaceutical carriers according to conventional procedures. These procedures may involve mixing granulating and compressing or dissolving the ingredients as appropriate to the desired preparation.

The pharmaceutical carrier(s) employed may be either solid or liquid. Exemplary solid carriers include lactose, sucrose, talc, gelatin, agar, pectin, acacia, magnesium stearate, stearic acid and the like. Exemplary liquid carriers include syrup, peanut oil, olive oil, water and the like. Similarly, the carrier(s) may include time-delay or time release materials known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation can be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an active agent can be dissolved in an aqueous solution of an organic or inorganic acid, such as 0.3 M solution of succinic acid or citric acid. If a soluble salt form is not available, the active agent may be dissolved in a suitable co-solvent or combinations of co-solvents. Examples of suitable co-solvents include, but are not limited to, alcohol, propylene glycol, polyethylene glycol 300, polysorbate 80, glycerin and the like in concentrations ranging from 0-60% of the total volume. The composition may also be in the form of a solution of a salt form of the active agent in an appropriate aqueous vehicle such as water or isotonic saline or dextrose solution.

It will be appreciated that the actual dosages of Compound 1 used in the compositions of this invention will vary according to the particular polymorphic form being used, the particular composition formulated, the mode of administration and the particular site, host and disease being treated. Those skilled in the art using conventional dosage-determination tests in view of the experimental data for an agent can ascertain optimal dosages for a given set of conditions. For oral administration, an exemplary daily dose generally employed is from about 0.001 to about 1000 mg/kg of body weight, more preferably from about 0.001 to about 50 mg/kg body weight, with courses of treatment repeated at appropriate intervals. Administration of prodrugs is typically dosed at weight levels that are chemically equivalent to the weight levels of the fully active form. In the practice of the invention, the most suitable route of administration as well as the magnitude of a therapeutic dose will depend on the nature and severity of the disease to be treated. The dose, and dose frequency, may also vary according to the age, body weight, and response of the individual patient. In general, a suitable oral dosage form may cover a dose range from 0.5 mg to 100 mg of active ingredient total daily dose, administered in one single dose or equally divided doses. A preferred amount of Compound 1 in such formulations is from about 0.5 mg to about 20 mg, such as from about 1 mg to about 10 mg or from about 1 mg to about 5 mg.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations that can be used pharmaceutically.

For oral administration, a polymorphic form of Compound 1 can be formulated readily by combining the active agent with pharmaceutically acceptable carriers known in the art. Such carriers enable the compounds of the invention to be formulated as tablets, pills, dragees, capsules, gels, syrups, slurries, suspensions and the like, for oral ingestion by a patient to be treated. Pharmaceutical preparations for oral use can be obtained using a solid excipient in admixture with the active agent, optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethylcellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration to the eye, the active agent is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and selera. The pharmaceutically acceptable ophthalmic vehicle may be, for example, an ointment, vegetable oil, or an encapsulating material. An active agent of the invention may also be injected directly into the vitreous and aqueous humor or subtenon.

Alternatively, the active ingredient may be in powder form for constitution with a suitable vehicle, e.g., sterile pyrogen-free water, before use. The compounds may also be formulated in rectal or vaginal compositions such as suppositories or retention enemas, e.g., containing conventional suppository bases such as cocoa butter or other glycerides.

In addition to the formulations described above, the polymorphic forms may also be formulated as a depot preparation. Such long-acting formulations may be administered by implantation (for example, subcutaneously or intramuscularly) or by intramuscular injection. Thus, for example, the polymorphic forms may be formulated with suitable polymeric or hydrophobic materials (for example, as an emulsion in an acceptable oil) or ion-exchange resins, or as sparingly soluble derivatives, for example, as a sparingly soluble salt.

Additionally, polymorphic forms of Compound 1 may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compound for a few weeks up to over 100 days.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

III. Methods of Using the Polymorphs of the Invention

Polymorphic forms of Compound 1 are useful for mediating the activity of protein kinases. More particularly, the polymorphic forms are useful as anti-angiogenesis agents and as agents for modulating and/or inhibiting the activity of protein kinases, such as the activity associated with VEGF, FGF, CDK complexes, TEK, CHK1, LCK, FAK, and phosphorylase kinase among others, thus providing treatments for cancer or other diseases associated with cellular proliferation mediated by protein kinases in mammals, including humans.

Therapeutically effective amounts of Compound 1 may be administered, typically in the form of a pharmaceutical composition, to treat diseases mediated by modulation or regulation of protein kinases. An "effective amount" is intended to mean that amount of an agent that, when administered to a mammal in need of such treatment, is sufficient to effect treatment for a disease mediated by the activity of one or more protein kinases, such as tyrosine kinases. Thus, a therapeutically effective amount of Compound 1 is a quantity sufficient to modulate, regulate, or inhibit the activity of one or more protein kinases such that a disease condition that is mediated by that activity is reduced or alleviated. "Treating" is intended to mean at least the mitigation of a disease condition in a mammal, such as a human, that is affected, at least in part, by the activity of one or more protein kinases, such as tyrosine kinases, and includes: preventing the disease condition from occurring in a mammal, particularly when the mammal is found to be predisposed to having the disease condition but has not yet been diagnosed as having it; modulating and/or inhibiting the disease condition; and/or alleviating the disease condition. Exemplary disease conditions include diabetic retinopathy, neovascular glaucoma, rheumatoid arthritis, psoriasis, age-related macular degeneration (AMD), and abnormal cell growth, such as cancer.

In one embodiment of this method, the abnormal cell growth is cancer, including, but not limited to, mesothelioma, hepatobilliary (hepatic and billiary duct), a primary or secondary CNS tumor, a primary or secondary brain tumor, lung cancer (NSCLC and SCLC), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, non hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In one embodiment of the present invention the cancer is lung cancer (NSCLC and SCLC), cancer of the head or neck, ovarian cancer, colon cancer, rectal cancer, cancer of the anal region, stomach cancer, breast cancer, cancer of the kidney or ureter, renal cell carcinoma, carcinoma of the renal pelvis, neoplasms of the central nervous system (CNS), primary CNS lymphoma, non hodgkins's lymphoma, or spinal axis tumors, or a combination of one or more of the foregoing cancers.

In a particular embodiment, the cancer is cancer of the thyroid gland, cancer of the parathyroid gland, pancreatic cancer, colon cancer, or renal cell carcinoma.

In another embodiment of said method, said abnormal cell growth is a benign proliferative disease, including, but not limited to, psoriasis, benign prostatic hypertrophy or restinosis.

This invention also relates to a method for the treatment of abnormal cell growth in a mammal which comprises administering to said mammal an amount of a polymorphic form of Compound 1 that is effective in treating abnormal cell growth in combination with an anti-tumor agent selected from the group consisting of mitotic inhibitors, alkylating agents, antimetabolites, intercalating antibiotics, growth factor inhibitors, cell cycle inhibitors, enzymes, topoisomerase inhibitors, biological response modifiers, antibodies, cytotoxics, antihormones, and anti-androgens.

EXAMPLES

The examples which follow will further illustrate the preparation of the distinct polymorphic forms of the invention, i.e. polymorphic Forms XXV and XVI of Compound 1, but are not intended to limit the scope of the invention as defined herein or as claimed below.

The following abbreviations may be used herein: THF (tetrahydrofuran); NMP (N-methylpyrrolidinone); Xantphos (9,9-Dimethyl-4,5-bis(diphenyl-phosphino)xanthene); Pd$_2$(dba)$_3$ (tris(dibenzylideneacetone)dipalladium(0)); and MeOH (methanol).

Example 1

Preparation and Characterization of Polymorphic Forms VIII, XVI, XXV and XLI of Compound 1

Forms XXV and XLI of Compound 1 can be prepared from Form XVI, which can be prepared from Form VIII, as indicated in the following examples.

a) Preparation of Form VIII

Form VIII is a THF solvate polymorphic form of Compound 1 that can be prepared during the final step of preparing Compound 1 as follows. Methods of preparing Compound 1 have been previously disclosed using Heck reaction methodology (e.g. WO 2006/048745 and U.S. 2006-0094881). To prepare Compound 1 in polymorphic Form VIII, Compound 1 was prepared as follows. The crude Compound 1 material from the Heck reaction (approximately 55 kg) was reslurried warm in THF (210 L) with 1,2-diaminopropane (13 kg) and then cooled for filtration. The filtered solids were washed with THF (210 L), dried under vacuum with heating to 40 to 70° C. and isolated to afford crude Compound 1 (Form VIII, THF solvate), (52.5 kg, 73%). Form VIII was characterized by PXRD as described previously and shown in FIG. 5.

b) Preparation of Form XVI

Form XVI is an isopropanol solvate polymorphic form of Compound 1 that can be prepared from Form VIII as follows. Form VIII (as prepared above) was dissolved (50 kg) in N-methylpyrrolidinone (150 L) and THF (optional, 50 L) with 1,2-diaminopropane (28.8 kg). The solution was heated and the solution was passed through a micron filter to remove any insoluble material. Methanol (300 L) was then added to the warm solution. The product crystallized from solution and heating was continued. After a period of time, additional methanol (400 L) was added. The suspension was cooled and stirred for at least 12 hours. The suspension was filtered, washed with isopropanol (150 L) and blown dry. The solids were reslurried in isopropanol (200 L) with heating. The suspension was then cooled, filtered, and washed with isopropanol (150 L). The resulting solids (Form XVI, isopropanol solvate) were dried under vacuum at 40 to 70° C. for at least 24 hours such that levels of residual isopropanol were below 5% by weight and isolated. Form XVI was characterized by PXRD as described previously and shown in FIG. 4.

c) Preparation of Form XXV

Form XXV is an anhydrous polymorphic form of Compound 1 that can be prepared from Form XVI as follows. Form XVI (as prepared above) was charged (11.9 kg, 1 equivalent) to a speck-free vessel. Note, it may be important to use a dish shaped vessel rather than a conical vessel, and that high agitation is used to ensure that good mixing is achieved in this step. The transformation will be heterogeneous.

Form XXV seed crystals were then charged (120 g, 0.01 equivalents) to the vessel. Note that this process has been successfully executed without any seed crystals as well. Ethanol (120 L) was then charged to the solids in the vessel, followed by heating to reflux (target 79° C., set jackets to approximately 85° C.). The resulting slurry was then held at reflux for at least 8 hours. Note, there is a strong correlation between higher reaction temperatures leading to more rapid polymorph conversion. This is due to the fact that the process is likely solubility limited. Note that at 90° C. and in 30 mL/g (relative to Form XVI input) of solvent the active pharmaceutical ingredient dissolves in the ethanol leading to a recrystallization process.

The slurry was then sampled to ensure that conversion to Form XXV was completed. If conversion is incomplete an ethanol solvate may be present with Form XXV. If conversion is not complete, continue heating for at least another 8 hours. Once the conversion was complete after about 24 hours, the reaction mixture was cooled down to 15-25° C.

The slurry was then stirred for at least 1 hour at ambient conditions. The material was then filtered, and the filtercake was washed with ethanol (36 L). The solids were then dried (to remove ethanol and other alcohols) under vacuum at less than 70° C. for a minimum of 12 hours. Form XXV crystals were then isolated (11.4 kg, 96% yield). Form XXV was characterized by PXRD, solid state NMR, and Raman spectroscopy as described previously and shown in FIGS. 1, 2, and 3.

Alternatively, Form XXV was prepared without seed crystals as follows. To the vessel was added 2.0 g of Compound 1 (Form XVI) and 40 mL ethanol (denatured with 1% methanol). The slurry was heated to 77-78° C. under nitrogen for 24 hours. The slurry was allowed to cool to room temperature, granulated for 1 hour, filtered and rinsed with absolute ethanol (4 mL). The white solids were allowed to dry in a vacuum oven at 50-55° C. for 16 hours. This afforded 1.6 g of Compound 1 (Form XXV) as a white solid.

d) Preparation of Form XLI

Form XLI is an anhydrous polymorphic form of Compound 1 that can be prepared from Form XVI as follows. Form XVI (as prepared above) was charged (11.9 kg, 1 equivalent) to a speck-free vessel. Note, it may be important to use a dish shaped vessel rather than a conical vessel, and that high agitation is used to ensure that good mixing is achieved in this step. The transformation will be heterogeneous.

Form XLI seed crystals were then charged (120 g, 0.01 equivalents) to the vessel. Note that this process has been successfully executed without any seed crystals as well. Ethanol (120 L) was then charged to the solids in the vessel, followed by heating to reflux (target 79° C., set jackets to approximately 85° C.). The resulting slurry was then held at reflux for at least 2 hours. Note, there is a strong correlation between higher reaction temperatures leading to more rapid polymorph conversion. This is due to the fact that the process is likely solubility limited. Note that at 90° C. and in 30 mL/g (relative to Form XVI input) of solvent the active pharmaceutical ingredient dissolves in the ethanol leading to a recrystallization process.

The slurry was then sampled to ensure that conversion to Form XLI was completed. If conversion is incomplete an ethanol solvate may be present with Form XLI. If conversion is not complete, continue heating for at least another 2 hours. Once the conversion was complete after about 24 hours, the reaction mixture was cooled down to 15-25° C.

The slurry was then stirred for at least 1 hour at ambient conditions. The material was then filtered, and the filtercake was washed with ethanol (36 L). The solids were then dried (to remove ethanol and other alcohols) under vacuum at less than 70° C. for a minimum of 12 hours. Form XLI crystals were then isolated (11.4 kg, 96% yield). Form XLI was characterized by PXRD and solid state NMR as described previously and shown in FIGS. 6, 7, and 8.

Alternatively, Form XLI was prepared without seed crystals as follows. To a vessel was added 4.0 kg of crude Compound 1 and 40 L of isopropanol. The suspension was heated to a temperature of 50 to 70° C. and held for 3 hours. After this time, the suspension was cooled to ambient conditions and filtered to isolate the solids. The wet cake was washed with 12 L of isopropanol and dried on the filter with a nitrogen bleed for about 2 hours and then were transferred to a tray dryer for further drying under vacuum with heating to 55 to 65° C. After about 18 hours, the solids were then recharged to the vessel with 40 L of absolute ethanol and were heated to a reflux (about 79° C.). The reaction mixture was distilled to remove approximately 12 L of solvent. The resulting reaction mixture was then heated at a reflux for an additional 2 hours. The mixture was then cooled to ambient conditions and stirred for about 1 hour. The solids were filtered and the wet cake was washed with 12 L of absolute ethanol. The solids were transferred to a tray dryer and dried under vacuum at 50 to 60° C. for about 24 hours. The solids were discharged to afford Compound 1, Form XLI, as a white crystalline solid, 3.8 kg.

Example 2

Preparation and Characterization of Polymorphic Form IX of Compound 1

Forms IX of Compound 1 can be prepared from Form IV as indicated in the following examples. Form IV is an anhydrous polymorphic form of Compound 1 that can be prepared as disclosed in U.S. 2006-0094763.

Preparation of Form IX

Form IX is a hydrate form of Compound 1 that can be prepared from Form IV as follows: Form IV was added (1 g) to a 1:1 isopropanol:water mixture (50 ml). The suspension was heated and stirred at 45° C. for two days, then allowed to cool to 25° C. The suspension was filtered, washed with 1:1 isopropanol:water and dried under vacuum at 40° C. for one day.

Example 3

Preparation and Characterization of Polymorphic Form XII of Compound 1

Form XII is an ethanol solvate polymorphic form of Compound 1 that can be prepared from Form XVI as follows. Form XVI (as prepared in Example 1) was added (1 g) to ethanol (100 ml). The solution was heated and stirred at 40° C. for two hours, then allowed to cool to 25° C. The suspension was filtered, washed with ethanol and dried under vacuum at 45° C. for three days.

Example 4

Preparation and Characterization of Polymorphic Form XV of Compound 1

Form XV is an ethanol solvate polymorphic form of Compound 1 that can be prepared from Form XVI as follows. Form XVI (as prepared in Example 1) was added (1 g) to ethanol (450 ml) and stirred at ambient temperature for one hour. The suspension was gravity filtered into an evaporation dish, and allowed to evaporate under a stream of nitrogen for several days to dryness.

Example 5

Preparation and Characterization of Amorphous Compound 1

Amorphous form of Compound 1 can be prepared from Form XLI as follows: Form XLI (as prepared above in Example 1) was added (135 mg) to a Wig-L-Bug® mixer/grinder (Model 30) with stainless steel ball. The solid was ground for 150 minutes to afford amorphous solid.

Example 6

Photochemical Stability of Form XLI and Form XXV Over Form IV

A photochemical comparative study of Form XLI, Form XXV, and Form IV was performed. The resulting data shows a significant improvement in stability of both Form XLI and Form XXV relative to Form IV. Improved stability of one polymorph over another is implicitly an advantage in pharmaceuticals. In the case of photochemical stability, special handling precautions or packaging to protect the compound against light, which could increase the cost of manufacture and storage, may be avoided with Form XXV and Form XLI. The enhanced stability of Form XXV and Form XLI will also significantly reduce the potential of photochemical degradation products appearing in pharmaceutical preparations (e.g. tablets) upon storage over time. The relative lack of photodegradation of Form XXV and Form XLI also reduces their potential to cause photosensitivity reactions in patients receiving the drug from exposure to sunlight.

Experimental Conditions:

Approximately 50 mg of each form was placed in 20 ml glass vials. The sample depth was <3 mm. The vials were covered with a quartz glass dish and placed in an Atlas Suntest XLS+ light box equipped with a 320 nm cutoff filter. The spectral output is similar to the ID65 emission standard, 320-800 nm (ID65 is the indoor indirect daylight ISO standard). The samples were exposed to artificial light equivalent to the International Conference on Harmonization (ICH) Guidelines for Photostability Testing of New Drug Substances, Option 1 exposure. The resulting data are tabulated below:

| Photochemical Stability under 1X ICH Option 1 light exposure: | |
|---|---|
| | Potency (wt/wt %) after light exposure |
| Form XXV | 100% |
| Form XLI | 89% |
| Form IV | 34% |

Example 7

Manufacturing Filtration Time of Form XLI and Form XXV Over Form IV

A comparison of the manufacturing filtration times of Form XLI, Form XXV, and Form IV was performed.

The resulting data shows a significant improvement in filtration times of Form XLI and Form XXV relative to Form IV. This may be attributable to a reduced tendency for particle agglomeration of Form XXV and Form XLI. This improvement results in a significant time reduction to filter the final product, which results in significant cost savings for the manufacturing process.

Experimental Conditions:

All three batches shown below, of approximately 20 kg scale, were filtered during manufacturing of compound of formula 1. The filter had a 0.25 m² filter area and a maximum usable cake capacity of 40 liters. All batches were filtered using the same equipment.

| | Filtration Time (hr) |
|---|---|
| Form XLI | 0.1 |
| Form XXV | 4.0 |
| Form IV | 25.9 |

While the invention has been illustrated by reference to specific and preferred embodiments, those skilled in the art will recognize that variations and modifications may be made through routine experimentation and practice of the invention. Thus, the invention is intended not to be limited by the foregoing description, but to be defined by the appended claims and their equivalents.

We claim:

1. A crystalline form of 6-[2-(methylcarbamoyl)phenylsulfanyl]-3-E-[2-(pyridin-2-yl)ethenyl]indazole, wherein said crystalline form has a powder X-ray diffraction pattern comprising a peak at diffraction angle (2θ) of 6.0±0.1 and further comprising at least one peak at diffraction angle (2θ) selected from 11.5±0.1, 21.0±0.1 and 26.9±0.1.

2. A crystalline form of 6-[2-(methylcarbamoyl)phenylsulfanyl]-3-E-[2-(pyridin-2-yl)ethenyl]indazole, wherein said crystalline form has a powder X-ray diffraction pattern comprising a peak at diffraction angle (2θ) of 6.0±0.1, 11.9±0.1 and 22.8±0.1.

3. A crystalline form of 6-[2-(methylcarbamoyl)phenylsulfanyl]-3-E-[2-(pyridin-2-yl)ethenyl]indazole, wherein said crystalline form has a powder X-ray diffraction pattern comprising a peak at diffraction angle (2θ) of 11.9±0.1 and 21.0±0.1, and further comprising at least one peak at diffraction angle (2θ) selected from 22.8±0.1, 23.1±0.1 and 26.9±0.1.

4. A crystalline form of 6-[2-(methylcarbamoyl)phenylsulfanyl]-3-E-[2-(pyridin-2-yl)ethenyl]indazole, wherein said crystalline form has a powder X-ray diffraction pattern comprising a peak at diffraction angle (2θ) of 11.5±0.1 and 15.6±0.1, and further comprising at least one peak at diffraction angle (2θ) selected from 16.2±0.1 and 16.5±0.1.

5. A crystalline form of 6-[2-(methylcarbamoyl)phenylsulfanyl]-3-E-[2-(pyridin-2-yl)ethenyl]indazole, wherein said crystalline form has a solid state NMR spectrum comprising $^{13}C$ chemical shifts at 150.1±0.2, 136.6±0.2, 135±0.2, 116.9±0.2 and 27.5±0.2 ppm.

6. A crystalline form of 6-[2-(methylcarbamoyl)phenylsulfanyl]-3-E-[2-(pyridin-2-yl)ethenyl]indazole, wherein said crystalline form has a powder X-ray diffraction pattern comprising a peak at diffraction angle (2θ) of 6.0±0.1 and 11.5±0.1 and wherein said crystalline form has a solid state NMR spectrum comprising $^{13}C$ chemical shifts at 150.1±0.2 and 27.5±0.2 ppm.

* * * * *